US009657069B2

(12) United States Patent
Yun et al.

(10) Patent No.: US 9,657,069 B2
(45) Date of Patent: May 23, 2017

(54) ANTI-CANCER COMPOSITIONS CONTAINING WNT DECOY RECEPTOR

(75) Inventors: Chae Ok Yun, Seoul (KR); Jung-Sun Lee, Seoul (KR)

(73) Assignee: GENEMEDICINE CO., LTD., Seoul (KR)

( * ) Notice: Subject to any disclaimer, the term of this patent is extended or adjusted under 35 U.S.C. 154(b) by 39 days.

(21) Appl. No.: 14/239,259

(22) PCT Filed: Aug. 16, 2012

(86) PCT No.: PCT/KR2012/006527
§ 371 (c)(1),
(2), (4) Date: Apr. 3, 2014

(87) PCT Pub. No.: WO2013/025064
PCT Pub. Date: Feb. 21, 2013

(65) Prior Publication Data
US 2014/0315825 A1    Oct. 23, 2014

(30) Foreign Application Priority Data

Aug. 18, 2011  (KR) .................. 10-2011-0082087

(51) Int. Cl.
    *C07K 14/435*    (2006.01)
    *C07K 14/71*     (2006.01)
    *A61K 38/17*     (2006.01)
    *A61K 31/7088*   (2006.01)
    *A61K 48/00*     (2006.01)

(52) U.S. Cl.
    CPC ........ *C07K 14/435* (2013.01); *A61K 31/7088* (2013.01); *A61K 38/179* (2013.01); *C07K 14/71* (2013.01); *A61K 48/005* (2013.01); *C12N 2710/10321* (2013.01); *C12N 2710/10343* (2013.01)

(58) Field of Classification Search
None
See application file for complete search history.

(56) References Cited

PUBLICATIONS

Merck Manual Colorectal Cancer accessed Aug. 19, 2015 at URL merckmanuals.com/home/skin_disorders/skin_cancers/melanoma.html?qt=melanoma&alt=sh).*
Merck Manual Breast Cancer accessed Aug. 19, 2015 at URL: merckmanuals.com/home/womens_health_issues/breast_disorders/breast_cancer.html.*
Merck Manual Thyroid Cancers, accessed Aug. 19, 2015, merckmanuals.com/professional/endocrine_and_metabolic_disorders/thyroid_disorders/thyroid_cancers.html).*
Merck Manuals Brain Tumors accessed Aug. 19, 2015 at URL http://www.merckmanuals.com/home/brain-spinal-cord-and-nerve-disorders/tumors-of-the-nervous-system/brain-tumors).*
International Search Report for PCT/KR2012/006527.
Liu, C-C. et al., "Cooperative Folding and Ligand-binding Properties ofLRP6 beta Propeller Domains", The Journal of Biological Chemistry, 2009, vol. 284, No. 22, pp. 15299-15307 (See abstract; p. 15299 left colunm; p. 15300 right colunm ("Generation of LRP6 BP Constructs"); pp. 15301-15302; p. 15305 right colunm-p. 15306; figures 1, 5-7.).
Russell, W. C., "Update on adenovirus and its vectors", Journal of General Virology, 2000, vol. 81, pp. 2573-2604. (See p. 2582 right colunm-p. 2583 left colunm; p. 2586 right column-p. 2587.).
Akiri, G. et al., "Wnt pathway aberrations including autocrine Wnt activation occur at high frequency in human non-small-cell lung carcinoma", Oncogene, 2009, vol. 28, pp. 2163-2172. (See abstract; figures 1-4; pp. 2166-2167.).

* cited by examiner

*Primary Examiner* — James H Alstrum Acevedo
*Assistant Examiner* — Tara Martinez
(74) *Attorney, Agent, or Firm* — Harness, Dickey & Pierce, P.L.C.

(57) ABSTRACT

The present invention relates to a composition for preventing or treating cancer comprising Wnt decoy receptor. The composition of the present invention or the expression product thereof inhibits cancer generation, growth, proliferation and metastasis, and induces apoptosis of cancer cells, by binding to Wnt ligand and blocking ligand-receptor interactions, therefore may be effectively used as an anti-cancer agent.

11 Claims, 21 Drawing Sheets

Replication-incompetent adenoviruses

Replication-competent adenoviruses

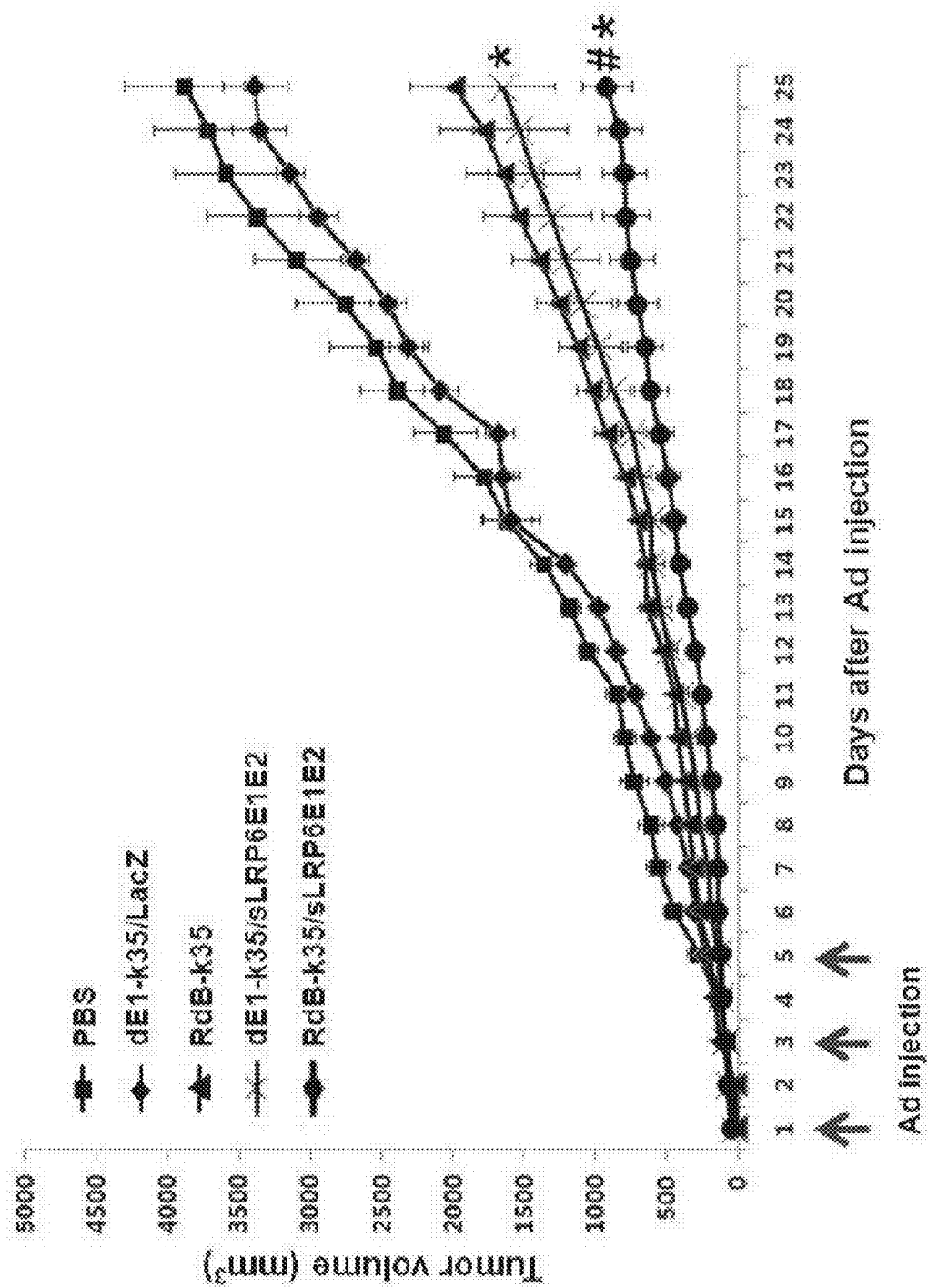

```
                        SEQUENCE LISTING

<160> NUMBER OF SEQ ID NOS: 2

<210> SEQ ID NO 1
<211> LENGTH: 1953
<212> TYPE: DNA
<213> ORGANISM: Artificial Sequence
<220> FEATURE:
<223> OTHER INFORMATION: sLRP6E1E2

<400> SEQUENCE: 1
atgggggccg tcctgaggag cctcctggcc tgcagcttct gtgtgctcct gagagcggcc      60
cctttgttgc tttatgcaaa cagacgggac ttgcgattgg ttgatgctac aaatggcaaa     120
gagaatgcta cgattgtagt tggaggcttg gaggatgcag ctgcggtgga ctttgtgttt     180
agtcatggct tgatatactg gagtgatgtc agcgaagaag ccattaaacg aacagaattt     240
aacaaaactg agagtgtgca gaatgttgtt gtttctggat tattgtcccc cgatgggctg     300
gcatgtgatt ggcttggaga aaaattgtac tggacagatt ctgaaactaa tcggattgaa     360
gtttctaatt tagatggatc tttacgaaaa gtttatttt ggcaagagtt ggatcaaccc     420
agagctattg ccttagatcc ttcaagtggg ttcatgtact ggacagactg gggagaagtg     480
ccaaagatag aacgtgctgg aatggatggt tcaagtcgct tcattataat aaacagtgaa     540
atttactggc caaatggact gactttggat tatgaagaac aaaagcttta tgggcagat     600 gcaaaactta atttcatcca caatcaaat ctggatggaa caaatcggca ggcagtggtt     660
aaaggttccc ttccacatcc ttttgccttg acgttatttg aggacatatt gtactggact     720
gactggagca cacactccat tttggcttgc aacaagtata ctggtgaggg tctgcgtgaa     780
atccattctg acatcttctc tcccatggat atacatgcct tcagccaaca gaggcagcca     840
aatgccacaa atccatgtgg aattgacaat ggggttgtt cccatttgtg tttgatgtct     900
ccagtcaagc ctttttatca gtgtgcttgc cccactgggg tcaaactcct ggagaatgga     960
aaaacctgca aagatggtgc cacagaatta ttgcttttag ctcgaaggac agacttgaga    1020
cgcatttctt tggatacacc agattttaca gacattgttc tgcagttaga agacatccgt    1080
catgccattg ccatagatta cgatcctgtg gaaggctaca tctactggac tgatgatgaa    1140
gtgagggcca tacgccgttc atttatagat ggatctggca gtcagtttgt ggtcactgct    1200
caaattgccc atcctgatgg tattgctgtg gactgggttg cacgaaatct ttattggaca    1260
```

-continued

```
gacactggca ctgatcgaat agaagtgaca aggctcaatg ggaccatgag gaagatcttg    1320
atttcagagg acttagagga accccgggct attgtgttag atcccatggt tgggtacatg    1380
tattggactg actggggaga aattccgaaa attgagcgag cagctctgga tggttctgac    1440
cgtgtagtat tggttaacac ttctcttggt tggccaaatg gtttagcctt ggattatgat    1500
gaaggcaaaa tatactgggg agatgccaaa acagacaaga ttgaggttat gaatactgat    1560
ggcactggga gacgagtact agtggaagac aaaattcctc acatatttgg atttactttg    1620
ttgggtgact atgtttactg gactgactgg cagaggcgta gcattgaaag agttcataaa    1680
cgaagtgcag agagggaagt gatcatagat cagctgcctg acctcatggg cctaaaggct    1740
acaaatgttc atcgagtgat tggttccaac ccctgtgctg aggaaaacgg gggatgtagc    1800
catctctgcc tctatagacc tcagggcctt cgctgtgctt gccctattgg ctttgaactc    1860
atcagtgaca tgaagacctg cattgtccca gaggctttcc ttttgttttc acggagagca    1920
gatatcagac gaatttctct ggaaacaaac aat                                  1953
```

<210> SEQ ID NO 2
<211> LENGTH: 651
<212> TYPE: PRT
<213> ORGANISM: Artificial Sequence
<220> FEATURE:
<223> OTHER INFORMATION: sLRP6E1E2

<400> SEQUENCE: 2

```
Met Gly Ala Val Leu Arg Ser Leu Leu Ala Cys Ser Phe Cys Val Leu
1               5                   10                  15

Leu Arg Ala Ala Pro Leu Leu Tyr Ala Asn Arg Arg Asp Leu Arg
            20                  25                  30

Leu Val Asp Ala Thr Asn Gly Lys Glu Asn Ala Thr Ile Val Val Gly
        35                  40                  45

Gly Leu Glu Asp Ala Ala Ala Val Asp Phe Val Phe Ser His Gly Leu
    50                  55                  60

Ile Tyr Trp Ser Asp Val Ser Glu Glu Ala Ile Lys Arg Thr Glu Phe
65                  70                  75                  80

Asn Lys Thr Glu Ser Val Gln Asn Val Val Val Ser Gly Leu Leu Ser
                85                  90                  95

Pro Asp Gly Leu Ala Cys Asp Trp Leu Gly Glu Lys Leu Tyr Trp Thr
            100                 105                 110

Asp Ser Glu Thr Asn Arg Ile Glu Val Ser Asn Leu Asp Gly Ser Leu
        115                 120                 125

Arg Lys Val Leu Phe Trp Gln Glu Leu Asp Gln Pro Arg Ala Ile Ala
    130                 135                 140

Leu Asp Pro Ser Ser Gly Phe Met Tyr Trp Thr Asp Trp Gly Glu Val
145                 150                 155                 160

Pro Lys Ile Glu Arg Ala Gly Met Asp Gly Ser Ser Arg Phe Ile Ile
                165                 170                 175

Ile Asn Ser Glu Ile Tyr Trp Pro Asn Gly Leu Thr Leu Asp Tyr Glu
            180                 185                 190

Glu Gln Lys Leu Tyr Trp Ala Asp Ala Lys Leu Asn Phe Ile His Lys
        195                 200                 205

Ser Asn Leu Asp Gly Thr Asn Arg Gln Ala Val Val Lys Gly Ser Leu
    210                 215                 220

Pro His Pro Phe Ala Leu Thr Leu Phe Glu Asp Ile Leu Tyr Trp Thr
225                 230                 235                 240
```

```
Asp Trp Ser Thr His Ser Ile Leu Ala Cys Asn Lys Tyr Thr Gly Glu
            245                 250                 255

Gly Leu Arg Glu Ile His Ser Asp Ile Phe Ser Pro Met Asp Ile His
            260                 265                 270

Ala Phe Ser Gln Gln Arg Gln Pro Asn Ala Thr Asn Pro Cys Gly Ile
            275                 280                 285

Asp Asn Gly Gly Cys Ser His Leu Cys Leu Met Ser Pro Val Lys Pro
        290                 295                 300

Phe Tyr Gln Cys Ala Cys Pro Thr Gly Val Lys Leu Leu Glu Asn Gly
305                 310                 315                 320

Lys Thr Cys Lys Asp Gly Ala Thr Glu Leu Leu Leu Ala Arg Arg
                325                 330                 335

Thr Asp Leu Arg Arg Ile Ser Leu Asp Thr Pro Asp Phe Thr Asp Ile
            340                 345                 350

Val Leu Gln Leu Glu Asp Ile Arg His Ala Ile Ala Ile Asp Tyr Asp
            355                 360                 365

Pro Val Glu Gly Tyr Ile Tyr Trp Thr Asp Asp Glu Val Arg Ala Ile
        370                 375                 380

Arg Arg Ser Phe Ile Asp Gly Ser Gly Ser Gln Phe Val Val Thr Ala
385                 390                 395                 400

Gln Ile Ala His Pro Asp Gly Ile Ala Val Asp Trp Val Ala Arg Asn
            405                 410                 415

Leu Tyr Trp Thr Asp Thr Gly Thr Asp Arg Ile Glu Val Thr Arg Leu
            420                 425                 430

Asn Gly Thr Met Arg Lys Ile Leu Ile Ser Glu Asp Leu Glu Glu Pro
            435                 440                 445

Arg Ala Ile Val Leu Asp Pro Met Val Gly Tyr Met Tyr Trp Thr Asp
        450                 455                 460

Trp Gly Glu Ile Pro Lys Ile Glu Arg Ala Ala Leu Asp Gly Ser Asp
465                 470                 475                 480

Arg Val Val Leu Val Asn Thr Ser Leu Gly Trp Pro Asn Gly Leu Ala
                485                 490                 495

Leu Asp Tyr Asp Glu Gly Lys Ile Tyr Trp Gly Asp Ala Lys Thr Asp
            500                 505                 510

Lys Ile Glu Val Met Asn Thr Asp Gly Thr Gly Arg Arg Val Leu Val
            515                 520                 525

Glu Asp Lys Ile Pro His Ile Phe Gly Phe Thr Leu Leu Gly Asp Tyr
        530                 535                 540

Val Tyr Trp Thr Asp Trp Gln Arg Arg Ser Ile Glu Arg Val His Lys
545                 550                 555                 560

Arg Ser Ala Glu Arg Glu Val Ile Ile Asp Gln Leu Pro Asp Leu Met
                565                 570                 575

Gly Leu Lys Ala Thr Asn Val His Arg Val Ile Gly Ser Asn Pro Cys
            580                 585                 590

Ala Glu Glu Asn Gly Gly Cys Ser His Leu Cys Leu Tyr Arg Pro Gln
        595                 600                 605

Gly Leu Arg Cys Ala Cys Pro Ile Gly Phe Glu Leu Ile Ser Asp Met
            610                 615                 620

Lys Thr Cys Ile Val Pro Glu Ala Phe Leu Leu Phe Ser Arg Arg Ala
625                 630                 635                 640

Asp Ile Arg Arg Ile Ser Leu Glu Thr Asn Asn
            645                 650
```

ANTI-CANCER COMPOSITIONS CONTAINING WNT DECOY RECEPTOR

CROSS REFERENCE TO RELATED APPLICATIONS AND CLAIM OF PRIORITY

This patent application is a National Phase application under 35 U.S.C. §371 of International Application No. PCT/KR2012/006527, filed Aug. 16, 2012, which claims priority to Korean Patent Application No. 10-2011-0082087, filed on Aug. 18, 2011, entire contents of which are incorporated herein by reference.

BACKGROUND OF THE INVENTION

Field of the Invention

The present invention relates to an anti-cancer composition containing Wnt decoy receptor which inhibits activation of Wnt signaling involved in tumor development.

Description of the Related Art

Lung cancer is highly aggressive and the most common cause of cancer-related deaths worldwide. In 2009, the American Cancer Society estimated that there were 219,440 new cases of lung cancer in the United States. Standard therapies such as surgery and radiation are not effective in many cases (1); however, an increased understanding of the molecular mechanisms of lung cancer has led to the development of promising new therapies (2). Although chemotherapy advances have improved overall survival for patients with aggressive non-small cell lung cancer, chemoresistance remains a major cause of treatment failure (3). Activating mutations in the epithelial growth factor receptor (EGFR) are present in a subset of lung adenocarcinomas, making these tumors highly resistant to EGFR tyrosine kinase inhibitors gefitinib and erlotinib (4, 5). Many aggressive lung cancers show alterations in various cancer-associated genes, including Wnt, K-ras, extracellular signal-regulated kinase (ERK), Akt, and cyclooxygenase-2, suggesting a different molecular pathway for carcinogenesis in lung adenocarcinomas (6-8).

The role of Wnt signaling in cancer was first suggested 20 years ago with the discovery of Wnt-1 as an integration site for mouse mammary tumor virus (9). Many studies have reported that altered expression of Wnt ligands, receptors, and extracellular antagonists are associated with cancer development/progression and stem cell self-renewal/differentiation (10). Expression of the Wnt ligand, low-density lipoprotein receptor-related protein 5 (LRP5), and LRP6 are upregulated in lung cancers, whereas Wnt antagonists that bind Wnt ligands to block interaction with receptors (e.g., Wnt inhibitory factor-1 (WIF-1), secreted Frizzled-related proteins (sFRP) and dickkopf proteins (DKK) are down-regulated or inactivated (11, 12). Accordingly, monoclonal antibodies and small interfering RNAs against Wnt and overexpression of Wnt antagonists suppress tumor growth in various in vitro and in vivo tumor models.

LRP6, a member of the LRP superfamily, is required for activation of the canonical Wnt signaling pathway, which leads to the stabilization and nuclear translocation of β-catenin, the key effector molecule (13). LRP6 consists of four distinct YWTD β-propeller/EGF-like domain pairs; the first and second YWTD domains (E1 and E2) are required for binding to Wnt (14-16). In the present study, we explored the therapeutic utility of a novel soluble Wnt receptor, sLRP6E1E2, which is composed of the LRP6 E1 and E2 regions. We examined the biological effects of sLRP6E1E2 binding to extracellular Wnt ligands and blocking ligand-receptor interactions. The results of the present invention provide direct evidence that specific Wnt ligand/receptor interactions have potential use as anticancer therapeutic agents.

Throughout this application, various publications and patents are referred and citations are provided in parentheses. The disclosures of these publications and patents in their entities are hereby incorporated by references into this application in order to fully describe this invention and the state of the art to which this invention pertains.

SUMMARY OF THE INVENTION

The present inventors have made intensive studies to develop a novel composition for cancer gene therapy with maximized inhibitory activity against cancer development/progression. As results, the present inventors have discovered that novel soluble Wnt receptor, sLRP6E1E2, inhibits activation of Wnt signaling pathway in a cancer cell through binding to Wnt 3a protein, thereby reducing tumor growth, proliferation and metastasis and inducing apoptosis of tumor cells.

Accordingly, it is an object of this invention to provide a composition for preventing or treating cancer.

It is another object of this invention to provide a method for preventing or treating cancer.

Other objects and advantages of the present invention will become apparent from the following detailed description together with the appended claims and drawings.

BRIEF DESCRIPTION OF THE DRAWINGS

FIG. 2 shows that decoy Wnt receptor sLRP6E1E2 reduces cytosolic β-catenin and T-cell factor transcriptional activity. FIG. 2b represents the result of TCF/LEF luciferase reporter assay in H460 and H322 cells. *$P<0.05$ versus PBS or dE1-k35/LacZ-transduced cells with or without Wnt3a.

FIG. 3 shows that decoy Wnt receptor sLRP6E1E2 decreases proliferation in human lung cancer cells.

FIG. 4 shows that decoy Wnt receptor sLRP6E1E2 induces apoptosis in human lung cancer cells.

FIG. 5 shows that decoy Wnt receptor sLRP6E1E2 inhibits tumor growth and characterization. FIG. 5a shows the tumor volume on days 1, 3, and 5 after tumors were injected with PBS (■), dE1-k35/LacZ (♦), RdB-k35 (▲), dE1-k35/sLRP6E1E2 (x), or RdB-k35/sLRP6E1E2 (•). Results are expressed as mean±SEM (n=7). *P<0.05 versus PBS-treated or dE1-k35-treated controls and versus dE1-k35/sLRP6E1E2. #P<0.01 versus PBS-treated or dE1-k35-treated controls.

FIG. 6 shows the disruption of cell-cell junctions and epithelial-to-mesenchymal transition in tumor cells by Wnt3a treatment.

FIG. 7 shows that Decoy Wnt receptor sLRP6E1E2 inhibits cancer cell migration and invasion, and modulates expression of epithelial-to-mesenchymal transition markers and MMPs. FIG. 7a represents the result of quantitative analysis of A549 lung cancer cell migration. Experiments were performed in triplicate, and results are expressed as mean±SEM. *P<0.05 versus PBS or dE1-k35/LacZ treated controls; **P<0.001 versus PBS or dE1-k35/LacZ with Wnt3a. FIG. 7b represents invasion of tumor cells quantified as number of cells in five fields of view per filter. Experiments were performed in triplicate, and results are expressed as mean±SEM. *P<0.05 versus PBS or dE1-k35/LacZ treated controls; **P<0.001 versus PBS or dE1-k35/LacZ with Wnt3a.

DETAILED DESCRIPTION OF THE INVENTION

Figure 1A:
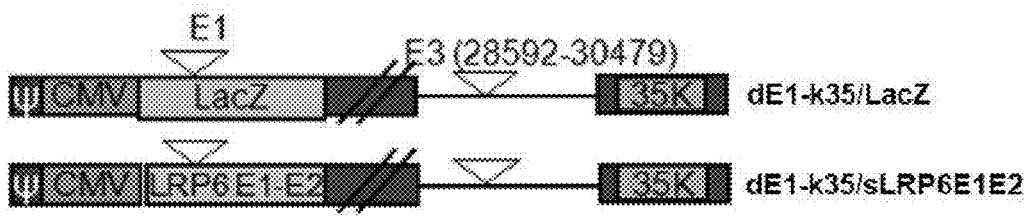
FIG. 1a is schematic representation of the genomic structure of Ad vectors used.
Figure 1A:
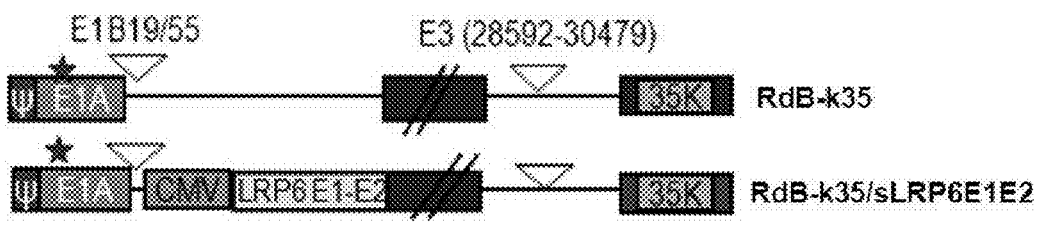

In one aspect of this invention, there is provided a composition for preventing or treating cancer, comprising a polypeptide having the amino acid sequence of SEQ ID NO:2.

In another aspect of this invention, there is provided a method for preventing or treating cancer comprising administering to a subject in need thereof a pharmaceutically effective amount of a polypeptide having the amino acid sequence of SEQ ID NO:2

The present inventors have made intensive studies to develop a novel composition for cancer gene therapy with maximized inhibitory activity against cancer development/progression. As results, the present inventors have discovered that novel soluble Wnt receptor, sLRP6E1E2, inhibits activation of Wnt signaling pathway in a cancer cell through binding to Wnt 3a protein, thereby reducing tumor growth, proliferation and metastasis and inducing apoptosis of tumor cells.

The term "polypeptide" as used herein, refers to a linear molecule formed by peptide bonds between amino acid residues. The SEQ ID NO:2 is the amino acid sequence of sLRP6E1E2 which is composed of the LRP6 E1 and E2 regions. According to the present invention, sLRP6E1E2 inhibits activation of Wnt signaling pathway which plays a critical role in cancer generation, growth, proliferation and metastasis, by blocking ligand-receptor interactions through binding to Wnt ligand.

More concretely, soluble Wnt receptor of the present invention reduces cytosolic β-catenin level and TCF transcriptional activity, inhibits cancer cell proliferation, induces cancer cell apoptosis, inhibits tumor growth, reduces expression of MMP-2 and MMP-9, which play a critical role in angiogenesis, tumor growth, and metastasis. Therefore, the composition of the present invention may be used as an anti-cancer agent effectively suppressing cancer progression The sLRP6E1E2 polypeptide of this invention may encompass sequences having substantial identity to the amino acid sequence of SEQ ID NO:2. Sequences having the substantial identity show at least 80%, more preferably at least 90%, most preferably at least 95% similarity to the amino acid sequence of sLRP6E1E2, as measured using one of the commonly used sequence comparison algorithms.

In addition, the sLRP6E1E2 polypeptide of this invention includes the protein having variant amino acid sequence as well as natural-occurring one. The variant of sLRP6E1E2 polypeptide refers to a protein of different sequence with deletion, insertion, conservative or non-conservative substitution or combination thereof in one or more amino acid residues. Such alteration of amino acid residues not to substantially impair protein activity is well known to one skilled in the art (H. Neurath, R. L. Hill, The Proteins, Academic Press, New York, 1979). Most common amino acid alteration includes Ala/Ser, Val/Ile, Asp/Glu, Thr/Ser, Ala/Gly, Ala/Thr, Ser/Asn, Ala/Val, Ser/Gly, Thy/Phe, Ala/Pro, Lys/Arg, Asp/Asn, Leu/Ile, Leu/Val, Ala/Glu and Asp/Gly, but not limited to.

Optionally, the Nkx3.2 protein may be modified by phosphorylation, sulfation, acrylation, glycosylation, methylation or farnesylation.

The sLRP6E1E2 polypeptide or its variants can be prepared by preparation from its natural source, chemical synthesis (Merrifleld, *J. Amer. chem. Soc.* 85:2149-2156, 1963) or recombinant methods based on DNA sequences (Sambrook, J. et al., *Molecular Cloning. A Laboratory Manual*, 3rd ed. Cold Spring Harbor Press (2001)).

In still another aspect of this invention, there is provided a composition for preventing or treating cancer, comprising a nucleotide sequence encoding the amino acid sequence of SEQ ID NO:2.

In still another aspect of this invention, there is provided a method for preventing or treating cancer comprising administering to a subject in need thereof a pharmaceutically effective amount of a nucleotide sequence encoding the amino acid sequence of SEQ ID NO:2.

According to a concrete embodiment, the nucleotide sequence comprises the nucleotide sequence of SEQ ID NO:1.

The SEQ ID NO:1 is the nucleotide sequence of sLRP6E1E2 which is composed of the E1 and E2 extracellular domains (Wnt-binding sites) of LRP6

It would be obvious to the skilled artisan that the nucleotide sequences used in this invention are not limited to those listed in the appended Sequence Listings.

For nucleotide sequences, the variations may be purely genetic, i.e., ones that do not result in changes in the protein product. This includes nucleic acids that contain functionally equivalent codons, or codons that encode the same amino acid, such as six codons for arginine or serine, or codons that encode biologically equivalent amino acids.

Considering biologically equivalent variations described hereinabove, the nucleic acid molecule of this invention may encompass sequences having substantial identity to them. Sequences having the substantial identity show at least 80%, more preferably at least 90%, most preferably at least 95% similarity to the nucleic acid molecule of this invention, as measured using one of the sequence comparison algorithms. Methods of alignment of sequences for comparison are well-known in the art. Various programs and alignment algorithms are described in: Smith and Waterman, *Adv. Appl. Math.* 2:482(1981); Needleman and Wunsch, *J. Mol. Bio.* 48:443(1970); Pearson and Lipman, *Methods in Mol. Biol.* 24: 307-31(1988); Higgins and Sharp, *Gene* 73:237-44 (1988); Higgins and Sharp, *CABIOS* 5:151-3(1989) Corpet et al., *Nuc. Acids Res.* 16:10881-90(1988) Huang et al., *Comp. Appl. BioSci.* 8:155-65(1992) and Pearson et al., *Meth. Mol. Biol.* 24:307-31(1994). The NCBI Basic Local Alignment Search Tool (BLAST) [Altschul et al., *J. Mol. Biol.* 215:403-10(1990)] is available from several sources, including the National Center for Biological Information (NBCI, Bethesda, Md.) and on the Internet, for use in connection with the sequence analysis programs blastp, blasm, blastx, tblastn and tblastx. It can be accessed at http://www.ncbi.nlm.nih.gov/BLAST/. A description of how to determine sequence identity using this program is available at http://www.ncbi.nlm.nih.gov/BLAST/blast_help.html.

According to a concrete embodiment, the nucleotide sequence is contained in a gene delivery system.

The term "gene delivery system" as used herein, refers to any forms of carriers that harbor and transport exogenous nucleic acid molecules to a host cell or tissue. The ideal gene delivery system should be harmless to human body, suitable for mass production, and capable of effective transportation of the target gene.

According to a more concrete embodiment, the gene delivery system is plasmid, recombinant adenovirus, adeno-associated virus (AAV), retrovirus, lentivirus, herpes simplex virus, vaccinia virus, measles virus, poxvirus, Semliki Forest virus, polymer, nanomaterial, lipospme or niosome.

The nucleotide sequence of this invention may be applied to all gene delivery system commonly used for gene therapy, concretely, plasmid, adenovirus (Lockett L J, et al., *Clin. Cancer Res.*, 3:2075-2080(1997)), adeno-associated virus (AAV, Lashford L S., et al., *Gene Therapy Technologies, Applications and Regulations* Ed. A. Meager, 1999), retrovirus (Gunzberg W H, et al., Retroviral vectors. *Gene Therapy Technologies, Applications and Regulations* Ed. A. Meager, 1999), lentivirus (Wang G. et al., *J. Clin. Invest.* 104(11):R55-62(1999)), herpes simplex virus (Chamber R., et al., *Proc. Natl. Acad. Sci USA*, 92:1411-1415(1995)), vaccinia virus (Puhlmann M. et al., *Human Gene Therapy*, 10:649-657(1999)), poxvirus (GCE, NJL, Krupa M, Esteban M., The poxvirus vectors MVA and NYVAC as gene delivery systems for vaccination against infectious diseases and cancer *Curr Gene Ther* 8(2):97-120(2008)), reovirus, measles virus, Semliki Forest virus, polymer (Hwang et al., In vitro and In vivo Transfection Efficiency of Human Osteoprotegerin Gene using Non-Viral Polymer Carriers., *Korean J. Bone Metab.* 13(2):119-128(2006)), lipospme (Methods in Molecular Biology, Vol 199, S. C. Basu and M. Basu (Eds.), Human Press 2002), nanomaterial or noisome. Most concretely, the gene delivery system of this invention is constructed by incorporating the nucleotide sequence of sLRP6E1E2 to adenoviruses.

i. Adenovirus

Adenovirus has been usually employed as a gene delivery vector because of its mid-sized genome, ease of manipulation, high titer, wide target-cell range and high infectivity. Both ends of the viral genome contains 100-200 bp ITRs (inverted terminal repeats), which are cis elements necessary for viral DNA replication and packaging. The E1 region (E1A and E1B) of genome encodes proteins responsible for the regulation of transcription of the viral genome and a few cellular genes. The E2 region (E2A and E2B) encodes proteins responsible for viral DNA replication.

Of adenoviral vectors developed so far, the replication incompetent adenovirus having the deleted E1 region is usually used. The deleted E3 region in adenoviral vectors may provide an insertion site for transgenes (Thimmappaya, B. et al., *Cell*, 31:543-551(1982); and Riordan, J. R. et al., *Science*, 245:1066-1073(1989)).

Therefore, the sequence of this invention may be inserted into the E1A promoter region. The term "deletion" with reference to viral genome sequences encompasses whole deletion and partial deletion as well.

According to a concrete embodiment, the recombinant adenovirus comprises deleted E1B and E3 region and the nucleotide sequence of SEQ ID NO:1 is inserted into the deleted E1B and E3 region.

In nature, adenovirus can package approximately 105% of the wild-type genome, providing capacity for about 2 extra kb of DNA (Ghosh-Choudhury et al., *EMBO J.*, 6:1733-1739(1987)). In this regard, the foreign sequences described above inserted into adenovirus may be further inserted into adenoviral wild-type genome.

The foreign genes delivered by the present adenoviral gene delivery system are episomal, and therefore, have low genotoxicity to host cells. Therefore, gene therapy using the adenoviral gene delivery system of this invention may be considerably safe.

ii. Retrovirus

Retroviruses capable of carrying relatively large exogenous genes have been used as viral gene delivery vectors in the senses that they integrate their genome into a host genome and have broad host spectrum.

In order to construct a retroviral vector, the cytokine gene is inserted into the viral genome in the place of certain viral sequences to produce a replication-defective virus. To produce virions, a packaging cell line containing the gag, pol and env genes but without the LTR (long terminal repeat) and Ψ components is constructed (Mann et al., *Cell*, 33:153-159(1983)). When a recombinant plasmid containing the cytokine gene, LTR and Ψ is introduced into this cell line, the Ψ sequence allows the RNA transcript of the recombinant plasmid to be packaged into viral particles, which are then secreted into the culture media (Nicolas and Rubinstein "Retroviral vectors," In: *Vectors: A survey of molecular cloning vectors and their uses*, Rodriguez and Denhardt (eds.), Stoneham: Butterworth, 494-513(1988)). The media containing the recombinant retroviruses is then collected, optionally concentrated and used for gene delivery system.

A successful gene transfer using the second-generation retroviral vector has been reported. Kasahara et al. (*Science*, 266:1373-1376(1994)) prepared variants of moloney murine leukemia virus in which the EPO (erythropoietin) sequence is inserted in the place of the envelope region, consequently, producing chimeric proteins having novel binding properties. Likely, the present gene delivery system can be constructed in accordance with the construction strategies for the second-generation retroviral vector.

iii. AAV Vector

Adeno-associated viruses are capable of infecting non-dividing cells and various types of cells, making them useful in constructing the gene delivery system of this invention. The detailed descriptions for use and preparation of AAV vector are found in U.S. Pat. Nos. 5,139,941 and 4,797,368. Research results for AAV as gene delivery systems are disclosed in LaFace et al, *Viology*, 162:483486 (1988), Zhou et al., *Exp. Hematol.* (*NY*), 21:928-933 (1993), Walsh et al, *J. Clin. Invest.*, 94:1440-1448(1994) and Flotte et al., *Gene Therapy*, 2:29-37(1995). Recently, an AAV vector has been approved for Phase I human trials for the treatment of cystic fibrosis.

Typically, a recombinant AAV virus is made by cotransfecting a plasmid containing the gene of interest (i.e., cytokine gene) flanked by the two AAV terminal repeats (McLaughlin et al., *J. Virol.*, 62:1963-1973(1988); Samulski et al., *J. Virol.*, 63:3822-3828(1989)) and an expression plasmid containing the wild type AAV coding sequences without the terminal repeats (McCarty et al., *J. Virol.*, 65:2936-2945(1991)).

iv. Other Viral Vectors

Other viral vectors may be employed as a gene delivery system in the present invention. Vectors derived from viruses such as vaccinia virus (Puhlmann M. et al., *Human Gene Therapy*, 10:649-657(1999); Ridgeway, "Mammalian expression vectors," In: *Vectors: A survey of molecular cloning vectors and their uses*. Rodriguez and Denhardt, eds. Stoneham: Butterworth, 467-492(1988)); Baichwal and Sugden, "Vectors for gene transfer derived from animal DNA viruses: Transient and stable expression of transferred genes," In: Kucherlapati R, ed. *Gene transfer*. New York: Plenum Press, 117-148(1986) and Coupar et al., Gene, 68:1-10(1988)), lentivirus (Wang G. et al., *J. Clin. Invest.*, 104(11):R55-62(1999)), herpes simplex virus (Chamber R., et al., *Proc. Natl. Acad. Sci USA*, 92:1411-1415(1995)), poxvirus (GCE, NJL, Krupa M, Esteban M., The poxvirus vectors MVA and NYVAC as gene delivery systems for vaccination against infectious diseases and cancer *Curr Gene Ther* 8(2):97-120(2008)), reovirus, measles virus, Semliki Forest virus, may be used in the present delivery systems for transferring the gene of interest into cells.

v. Polymer

Polymer vectors widely used as non-viral gene delivery system include PEG, PEI, PLL, gelatin, chitosan (Carreno G B, Duncan R. Evaluation of the biological properties of soluble chitosan and chitosan microspheres. *Int J Pharm* 148:231-240(1997)) PLL (poly-LLysine) (Maruyama A, Ishihara T, Kim J S, Kim S W, Akaike T. Nanoparticle DNA carrier with poly (L-lysine) grafted polysaccharide copolymer and poly (D,Llactide). *Bioconjugate Chem* 8:735-742 (1997)) and PEI (polyethyleneamine) (Abdallah B, Hassan A, Benoist C, Goula D, Behr J P, Demeneix B A. A powerful nonviral vector for in vivo gene transfer into the adult mammalian brain: Polyethyleneimine. *Human Gene Ther* 7:1947-1954(1996)). The advantages of polymer vector lie on low occurrence of immune response and acute toxicity, and simple preparation enabling mass production.

vi. Liospme and Niosome

Liposomes are formed spontaneously when phospholipids are suspended in an excess of aqueous medium. Liposome-mediated nucleic acid delivery has been very successful as described in Nicolau and Sene, *Biochim. Biophys. Acta*, 721:185-190(1982) and Nicolau et al., *Methods Enzymol.*, 149:157-176(1987). Example of commercially accessible reagents for transfecting animal cells using liposomes includes Lipofectamine (Gibco BRL). Liposomes entrapping the nucleotide sequence of interest interact with cells by mechanism such as endocytosis, adsorption and fusion and then transfer the sequences into cells.

Niosome is a bilayer vehicle composed of mixture of non-ionic surfactant and cholesterol which may encapsulate polar and non-polar material. Niosome has osmotic activity, higher stability compared to liposome. The surfactant used for the preparation of liposome is more easy in storage and handling.

The introduction into host cell of the gene delivery system can be performed through various methods known to those skilled in the art.

Where the present gene delivery system is constructed on the basis of viral vector construction, the contacting is performed as conventional infection methods known in the art. The infection of hosts using viral vectors is well described in the above-cited publications.

Where the gene delivery system of the present invention is naked recombinant DNA molecule or plasmid, it can be injected into the host cell by micro-injection (Capecchi, M. R., *Cell*, 22:479(1980); and Harland and Weintraub, *J. Cell Biol.* 101:1094-1099(1985)), calcium phosphate precipitation method (Graham, F. L. et al., *Virology*, 52:456(1973); and Chen and Okayama, *Mol. Cell. Biol.* 7:2745-2752 (1987)), electroporation (Neumann, E. et al., *EMBO J.*, 1:841(1982); and Tur-Kaspa et al., *Mol. Cell Biol.*, 6:716-718(1986)), liposome-mediated infection method (Wong, T. K. et al., *Gene*, 10:87(1980); Nicolau and Sene, *Biochim. Biophys. Acta*, 721:185-190 (1982); and Nicolau et al., *Methods Enzymol.*, 149:157-176 (1987)), DEAE-dextran treatment (Gopal, *Mol. Cell Biol.*, 5:1188-1190 (1985)), and gene bombardment (Yang et al., Proc. Natl. Acad. Sci., 87:9568-9572 (1990)).

According to the most concrete embodiment, the gene delivery system is recombinant adenovirus.

According to a concrete embodiment, the recombinant adenovirus comprises deleted E1B and E3 region and the nucleotide sequence of SEQ ID NO:1 is inserted into the deleted E1B and E3 region.

According to a concrete embodiment, the cancer prevented or treated by the composition of the present invention is lung cancer.

According to a concrete embodiment, the composition of the present invention inhibits activation of Wnt signaling pathway in a cancer cell.

According to a more concrete embodiment, the composition of the present invention inhibits activation of Wnt signaling pathway in a cancer cell through binding of the polypeptide having the amino acid sequence of SEQ ID NO:2 to Wnt 3a protein.

According to the present invention, sLRP6E1E2-transfected cell shows lower level of Wnt 3a and LPR6 proteins compared to controls, suggesting that LPR6 E1-E2 domains of sLRP6E1E2 effectively bind to Wnt 3a, thereby inhibit Wnt signaling which is involved in cancer progression.

Since the composition of the present invention is highly effective in reducing cancer cell growth and proliferation, and inducing apoptosis of cancer cells, it is useful in treating tumor-related diseases, including stomach cancer, lung cancer, breast cancer, ovarian cancer, liver cancer, brain cancer, prostate cancer, sarcoma, bronchogenic cancer, nasopharyngeal cancer, laryngeal cancer, pancreatic cancer, bladder cancer, colon cancer, and uterine cervical cancer.

Concretely, the cancer prevented or treated by the composition of the present invention is lung cancer.

The term "treatment" as used herein, refers to (i) prevention of tumorigenesis; (ii) suppression and curing of tumor-related diseases or disorders by eradicating tumor cells; and (iii) alleviation of tumor-related diseases or disorders by eradicating tumor cells.

The pharmaceutically acceptable carrier which may be contained in the composition of the present invention is commonly used in pharmaceutical formulations including but is not limited to, lactose, dextrose, sucrose, sorbitol, mannitol, starch, rubber arable, potassium phosphate, arginate, gelatin, potassium silicate, microcrystalline cellulose, DMSO, polyvinylpyrrolidone, cellulose, water, syrups, methylcellulose, methylhydroxy benzoate, propylhydroxy benzoate, talc, magnesium stearate, and mineral oils. The composition of the present invention may further include a lubricant, a humectant, a sweetener, a flavoring agent, an emulsifier, a suspending agent, and a preservative.

The composition of the present invention may be administered orally or parenterally, and preferably, administered parenterally. For parenteral administration, it may be administered intravenously, intraperitoneally, intramuscularly, intradermally or topically. The composition of the present invention may be administered intraperitoneally in ovarian cancer, intravenously in liver cancer, injected directly to tumor mass in breast cancer, directly administered by rectal injection in colon cancer, and directly administered via catheter in bladder cancer.

A suitable dosage amount of the pharmaceutical composition of the present invention may vary depending on pharmaceutical formulation methods, administration methods, the patient's age, body weight, sex, pathogenic state, diet, administration time, administration route, an excretion rate and sensitivity for a used pharmaceutical composition and physicians of ordinary skill in the art can determine an effective amount of the pharmaceutical composition for desired treatment. Generally, the pharmaceutical composition of the present invention comprises $1\times10^5$-$1\times10^{15}$ pfu/ml of a recombinant adenovirus and $1\times10^{10}$ pfu of a recombinant adenovirus is typically injected once every other day over two weeks.

According to the conventional techniques known to those skilled in the art, the composition of the present invention may be formulated with pharmaceutically acceptable carrier and/or vehicle as described above, finally providing several forms a unit dose form and a multi-dose form. Non-limiting examples of the formulations include, but not limited to, a solution, a suspension or an emulsion in oil or aqueous medium, an extract, an elixir, a powder, a granule, a tablet and a capsule, and may further comprise a dispersion agent or a stabilizer.

The pharmaceutical composition comprising the recombinant adenovirus according to the present invention may be utilized alone or in combination with typical chemotherapy or radiotherapy. Such combination therapy may be more effective in treating cancer. The chemotherapeutic agents useful for the combination therapy include cisplatin, carboplatin, procarbazine, mechlorethamine, cyclophosphamide, ifosfamide, melphalan, chlorambucil, bisulfan, nikosourea, dactinomycin, daunorubicin, doxorubicin, bleomycin, plicomycin, mitomycin, etoposide, tamoxifen, taxol, transplatinum, 5-fluorouracil, vincristin, vinblastin and methotrexate. Examples of the radiotherapy useful for the combination therapy include X-ray illumination and γ-ray illumination.

Cell therapy that may be combined with the present invention includes dendritic cells, NK (Natural Killer) cells, TIL (Tumor Infiltrating Lymphocytes) and CTL (Cytotoxic T Lymphocytes).

The features and advantages of the present invention will be summarized as follows:

(a) The present invention provides a composition for preventing or treating cancer comprising Wnt decoy receptor.

(b) The composition of the present invention or the expression product thereof inhibits cancer generation, growth, proliferation and metastasis, and induces apoptosis of cancer cells, by binding to Wnt ligand and blocking ligand-receptor interactions, therefore may be effectively used as an anti-cancer agent.

The present invention will now be described in further detail by examples. It would be obvious to those skilled in the art that these examples are intended to be more concretely illustrative and the scope of the present invention as set forth in the appended claims is not limited to or by the examples.

Example

Materials and Methods

Materials

Polyclonal antibodies against MAPK kinase (MEK1/2), p44/42 mitogen-activated protein kinase (MAPK; Erk1/2), mTOR, phosphatidylinositol 3-kinase (PI3K) and Aid, and monoclonal antibodies against Wnt3a, Dvl2, Axin, glycogen synthase kinase (GSK3-β, poly (ADP-ribose) polymerase (PARP), and cleaved caspase-3 were purchased from Cell Signaling Technology (Beverly, Mass.). Antibodies against epithelial-to-mesenchymal transition (EMT)-related molecules β-catenin and E-cadherin were obtained from Cell Signaling Technology. Antibodies against cyclin D1 (H-295), cytochrome c (C-20 for Western blot analysis), and LRP6 (C-10), and protein A/G agarose beads were purchased from Santa Cruz Biotechnology (Santa Cruz, Calif.). Monoclonal antibody against caspase-3 was from StressGen Biotechnologies (Victoria, BC). Polyclonal antibody against cytochrome c (6H2.B4 for Immunohistochemistry) was from BD Pharmingen (San Diego, Calif.). Alexa Fluor 488-conjugated and Alexa Fluor 568-conjugated anti-rabbit IgG antibodies were obtained from Invitrogen (Carlsbad, Calif.). DAPI (1 µg/ml), Hoechst 33342, and tetramethylrhodamine isothiocyanate (TRITC)-conjugated phalloidin were from Sigma (St. Louis, Mo.). Purified Wnt3a protein was purchased from R&D Systems (Minneapolis, Minn.).

Generation of Adenoviral Vectors Expressing Soluble LRP6 Receptor

To study the biochemical function of soluble LRP6 receptor (sLRP6E1E2), we generated constructs of the E1 and E2 extracellular domains (Wnt-binding sites) of LRP6 (17) and FLAG-tagged sLRP6E1E2 was subcloned into a pCA14 shuttle vector (18). This pCA14-sLRP6E1E2 vector was co-transformed with a replication-incompetent adenovirus 5/35 chimeric vector (dE1-k35) or replication-competent chimeric oncolytic adenovirus vector (RdB-k35) (19), generating pdE1-k35/sLRP6E1E2 and pRdB-k35/sLRP6E1E2, respectively. These recombinant plasmids were transfected into HEK293 cells to generate dE1-k35/sLRP6E1E2 and RdB-k35/sLRP6E1E2. The replication-incompetent dE1-k35/LacZ and replication-competent oncolytic RdB-k35 vectors were used as negative controls (20) (FIG. 1A). All viruses were obtained as previously described (21).

Luciferase Reporter Assay for β-Catenin Activity

TOPflash and FOPflash luciferase reporter vectors (Upstate Biotechnology, Lake Placid, N.Y.) were used to measure β-catenin/T-cell factor (TCF) signaling activity. A549, H322, and H460 cells were seeded and transfected with 0.3 µg TOPflash (containing wild-type TCF binding sites) or FOPflash (containing mutated TCF binding sites) negative control with dE1-k35/LacZ or dE1-k35/sLRP6E1E2 (20, 50 MOI). After 12 hr, the medium was replaced with 1% DMEM with or without 100 ng/ml of Wnt3a, and the cells were incubated for another 24 hr. Cell extract was then analyzed using the Dual-Luciferase Reporter Assay System (Promega, Madison, Wis.).

Cell Proliferation Assay

The cell proliferation assay was determined by 3-(4,5-dimethylthiazol-2-yl)-2,5-diphenyl-tetrazolium bromide (MTT) assay (Sigma) (19). A549 and H322 cells were seeded in 24-well plates ($2 \times 10^4$ cells/well). After 24 hr, cells were treated with PBS, dE1-k35/LacZ, or dE1-k35/sLRP6E1E2. The next day, cells were stimulated with or without recombinant Wnt3a (100 ng/ml) for an additional 48 hr. Absorbance at 540 nm was read on a microplate reader.

Western Blotting and Immunoprecipitation

Cells cultured in DMEM with 1% fetal bovine serum in 100-mm plates were transduced with dE1-k35/LacZ or dE1-k35/sLRP6E1E2. The next day, cells were treated with or without Wnt3a (100 ng/ml) for 16 hr Immunoblotting was performed as described previously (19).

Immunofluorescence Assay

For immunofluorescence microscopy, cultured cells were fixed and permeabilized. The samples were blocked and then incubated with E-cadherin, β-catenin, or anti-cytochrome c primary antibodies. Staining was visualized by Alexa Flour 488-conjugated goat anti-rabbit IgG secondary antibody. The final antibody treatment also contained TRITC-conjugated phalloidin and Hoechst 33342 or DAPI stain (both at 1 µg/ml, Sigma) for nuclear staining. The cells were viewed under a confocal laser-scanning microscope (LSM510, Carl Zeiss MicroImaging, Thornwood, N.Y.).

Mitochondrial Fractionation and Western Blotting

Mitochondrial fractions were prepared using the Qproteome mitochondria isolation kit (QIAGEN, Hilden, Germany) following the manufacturer's instructions. Cells washed and suspended with ice-cold lysis buffer. After 10-min incubation, lysate was centrifuged, and the supernatant containing cytosolic proteins was removed. The pellet containing nuclei, cell debris, and unbroken cells was resuspended with ice-cold disruption buffer and centrifuged, and the supernatant (microsomal fraction) was transferred to a clean microtube. The resulting pellet containing mitochondria was washed with the mitochondria storage buffer and centrifuged. Western blotting was performed with the rabbit anti-cytochrome c antibody using the procedure described above.

Cytochrome c Immunostaining

A549 cells were plated in two-chamber slides ($3 \times 10^4$ cells/chamber; Nunc, Naperville, Ill.) and transduced with PBS, dE1-k35/LacZ, or dE1-k35/sLRP6E1E2 after treatment with or without Wnt3a. The next day, cells were fixed and incubated with medium containing 250 nM MitoTracker Red mitochondria stain (Molecular Probes, Eugene, Oreg.) for 30 min at room temperature. Cells were then incubated with 0.5 mg/ml anti-cytochrome c antibody. Next day, staining was visualized by Alexa Flour 488-conjugated goat anti-mouse IgG antibody. After washing, the slides were stained with Hoechst 33258 (1 mg/ml) for nuclear staining.

Anti-Tumor Effects in Human Xenograft Model

Human non-small cell lung cancer xenograft was established in 6- to 8-week-old male athymic nu/nu mice (Charles River Japan, Yokohama, Japan) by subcutaneous implantation of $1 \times 10^7$ H460 cells in the abdomen. When tumor volumes reached approximately 80-100 mm$^3$, the mice were divided five groups with similar mean tumor volumes. Adenoviral vectors were administered intratumorally ($2 \times 10^{10}$ viral particles/mouse) on the first day of treatment (day 1) and days 3 and 5. Tumor volume (V) was calculated as $V = 0.52 \times a^2 \times b$ (a, smallest superficial diameter; b, largest superficial diameter).

Tumor Histology and Immunohistochemistry

Tumor tissue was fixed and embedded in paraffin wax for histologic examination and immunohistochemical staining. Representative sections were stained with hematoxylin and eosin and examined by light microscopy. To quantify capillary density and Wnt expression, the tumor sections were stained with anti-mouse CD31 IgG (BD Pharmingen), anti-rabbit β-catenin IgG (Cell Signaling Technology), or anti-mouse Wnt3a IgG (Santa Cruz Biotechnology). Positive immunoreactivity was visualized with ABC-peroxidase kits (ChemMate™ DAKO Envision™ Detection kit; DAKO).

Migration and Invasion Assay

In vitro migration assays were performed as described previously (23). Conditioned media was obtained from A549 cells transduced with PBS, dE1-k35/LacZ, or dE1-k35/sLRP6E1E2 after treatment with or without Wnt3a and placed in the bottom Transwell chamber. A549 cells were then plated on the upper chamber ($7 \times 10^4$ cells/well). Cultures were incubated at 37° C. for 4 hr, fixed, and stained with hematoxylin and eosin. In vitro Matrigel invasion assays were performed using bio-coat cell migration chambers. Filters (8-µm pore) were coated with Matrigel basement membrane matrix (37 mg/filter; BD Biosciences, San Jose, Calif.), and the experiment was performed as described for the cell migration assay.

Reverse Transcription (RT)-PCR

Briefly, total RNA (1 µg) was isolated using the RNeasy Mini Kit (QIAGEN, Valencia, Calif.) and cDNA was synthesized with oligo-dT primers and M-MLV reverse transcriptase (Invitrogen). Polymerase chain reaction (PCR) was carried out using cDNA (25 ng) as a template and the following PCR primers: matrix metalloproteinase (MMP)2, forward 5'-CTCAGATCCGTGGTGAGATCT-3', reverse 5'-CTTTGGTTCTCCAGCTTCAGG-3', MMP9, forward 5'-ATCCAGTTTGGTGTCGCGGAGC-3', reverse 5'-GAAGGGGAAGACGCACAGCT-3', E-cadherin, 5'-ACGATGATGTGAACACCTACA-3', reverse 5'-ATGCCATCGT TGTTCACTGCA-3', Vimentin, forward 5'-TGGCACGTCTTGACCTTGAA-3', reverse 5'-GGTCATCGTGATGCTGAGAA-3', β-catenin, forward 5'-GCTGATTTGATGGAGTTGGA-3', reverse 5'-TCAGCTACTTGTTCTTGAGTGAA-3', β-actin, forward 5'-CCTTCCTGGGCATGGAGTCCT-3', reverse 5'-GGAGCAATGATCTTGATCTT-3'.

Statistical Analysis

Results are expressed as mean±standard error of the mean (SEM). Group results were compared by one-way analysis of variance, followed by post hoc Student's t-test for unpaired observations or Bonferroni's correction for multiple comparisons when appropriate. $P<0.05$ was considered significant.

Results

Figure 1B:
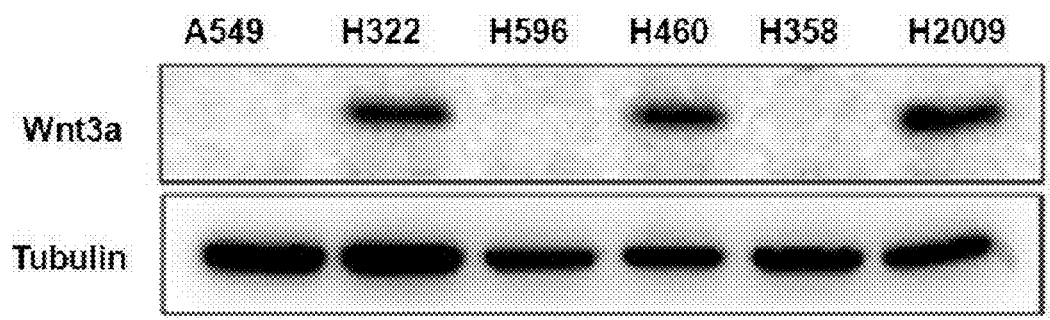
FIG. 1b shows endogenous Wnt3a expression in several human lung cancer cell lines.
Figure 1C:
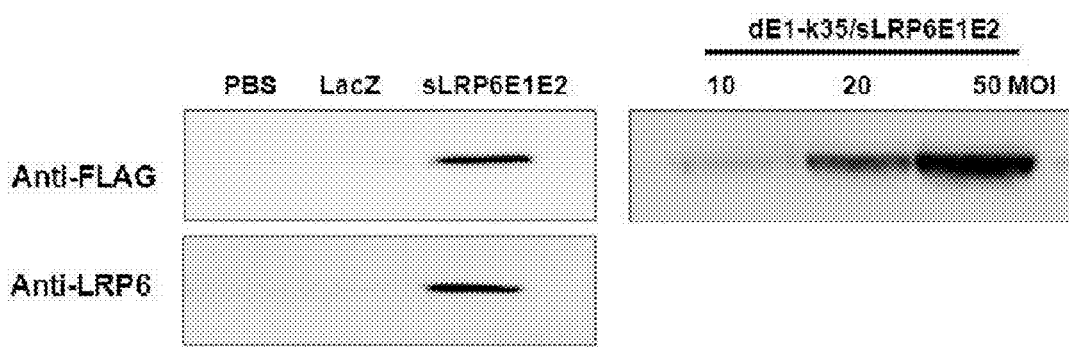
FIG. 1c shows secretion and expression of sLRP6E1E2. Cell culture supernatants were assessed with FLAG- or LRP6-specific Ab. (d) H322 and H460 cells were transduced with dE1-k35/LacZ or dE1-k35/sLRP6E1E2 (50 MOI) for 48 hr. Cell lysates were immunoprecipitated with antisera against Wnt3a (IP: Wnt3a) or LRP6 (IP: LRP6) followed by western blot (WB) analysis with the same antibodies.

Soluble Wnt Decoy Receptor is Expressed in Lung Cancer Cell Lines and Binds to Wnt3a Endogenous Wnt3a levels were assessed in six non-small cell lung cancer cell lines (A549, H322, H596, H460, H358, and H2009) by western blot analysis. Wnt3a was more strongly expressed in H322, H460, and H2009 cells than in other cell lines (FIG. 1b); therefore, H322 and H460 cells were selected to evaluate the ability of the soluble Wnt decoy receptor (sLRP6E1E2) to inhibit Wnt signaling. Expression of sLRP6E1E2 from dE1-k35/sLRP6E1E2-transduced A549 cells was confirmed by western blot analysis using anti-FLAG and anti-LRP6 antibodies (FIG. 1c). Secretion of sLRP6E1E2 from dE-k35/sLRP6E1E2-transduced cells was dose-dependent.

Figure 1D:
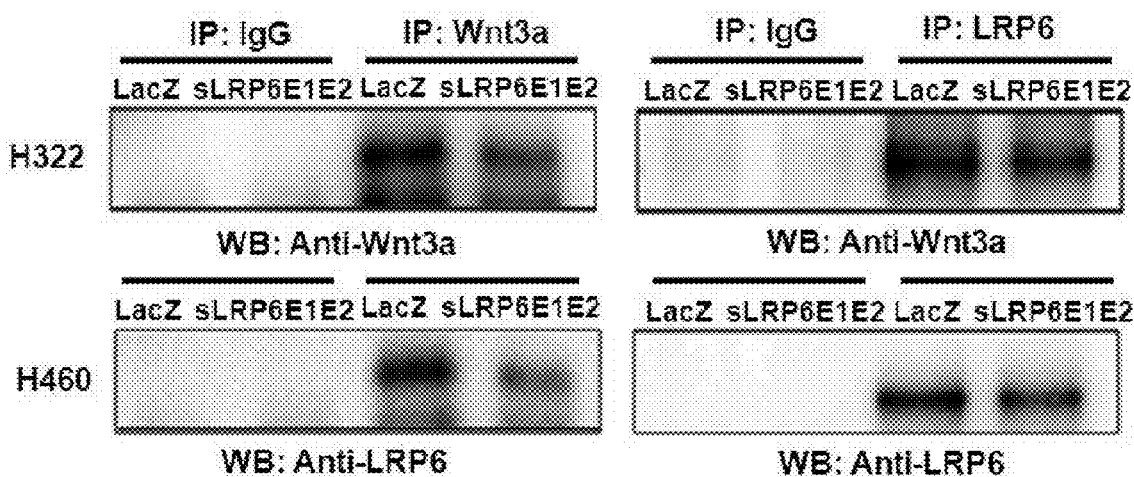
FIG. 1 represents characterization of the decoy Wnt receptor sLRP6E1E2.

Next, binding of sLRP6E1E2 to Wnt3a was assessed in cells transduced with dE1-k35/LacZ or dE1-k35/sLRP6E1E2. Cell lysates were immunoprecipitated with anti-Wnt3a or anti-LRP6 antibodies and analyzed by western blot. As shown in FIG. 1D, Wnt3a and LRP6 protein levels were lower in cells transduced with dE1-k35/sLRP6E1E2 than in cells transduced with dE1-k35/LacZ, indicating that the LRP6 E1-E2 domains efficiently bind to Wnt3a.

Figure 2A:
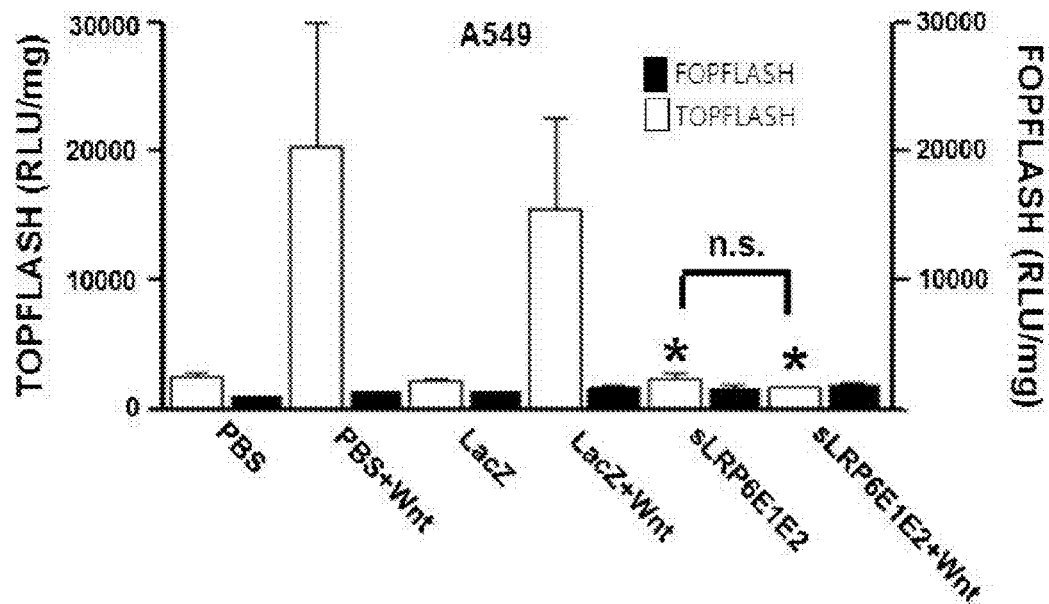
FIG. 2a represents the result of TCF/LEF luciferase reporter assay in A549 cells. *$P<0.05$ versus dE1-k35/LacZ-transduced or PBS-treated cells.
Figure 2B:
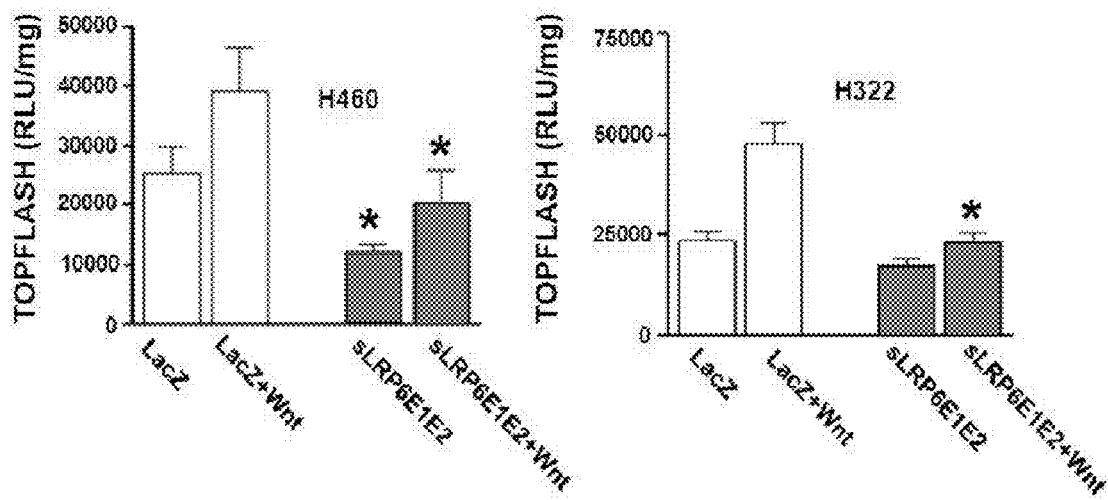

Decoy Wnt Receptor Decreases Cytosolic β-Catenin Level and TCF Transcriptional Activity Because sLRP6E1E2 binds to Wnt3a, we determined its effect on β-catenin using a luciferase reporter system activated by β-catenin/TCF (24). As shown in FIG. 2A, luciferase activity was low in A549 cells transduced with dE1-k35/LacZ or dE1-k35/sLRP6E1E2 in the absence of Wnt3a. Wnt3a treatment increased luciferase expression approximately 7- to 8-fold in control cells, but not in dE1-k35/sLRP6E1E2-transduced cells. In the absence of Wnt3a, luciferase activity was reduced by dE1-k35/sLRP6E1E2 in H460 (48%) and H322 (12%) cells compared with dE1-k35/LacZ controls (FIG. 2B; $P<0.05$). Wnt3a stimulation increased luciferase activity in H460 (53%) and H322 (102%) cells transduced with dE1-k35/LacZ, but luciferase activity was significantly lower in dE1-k35/sLRP6E1E2-transduced H460 (48%) and H322 (52%) cells compared with dE1-k35/LacZ ($P<0.05$).

Figure 2C:
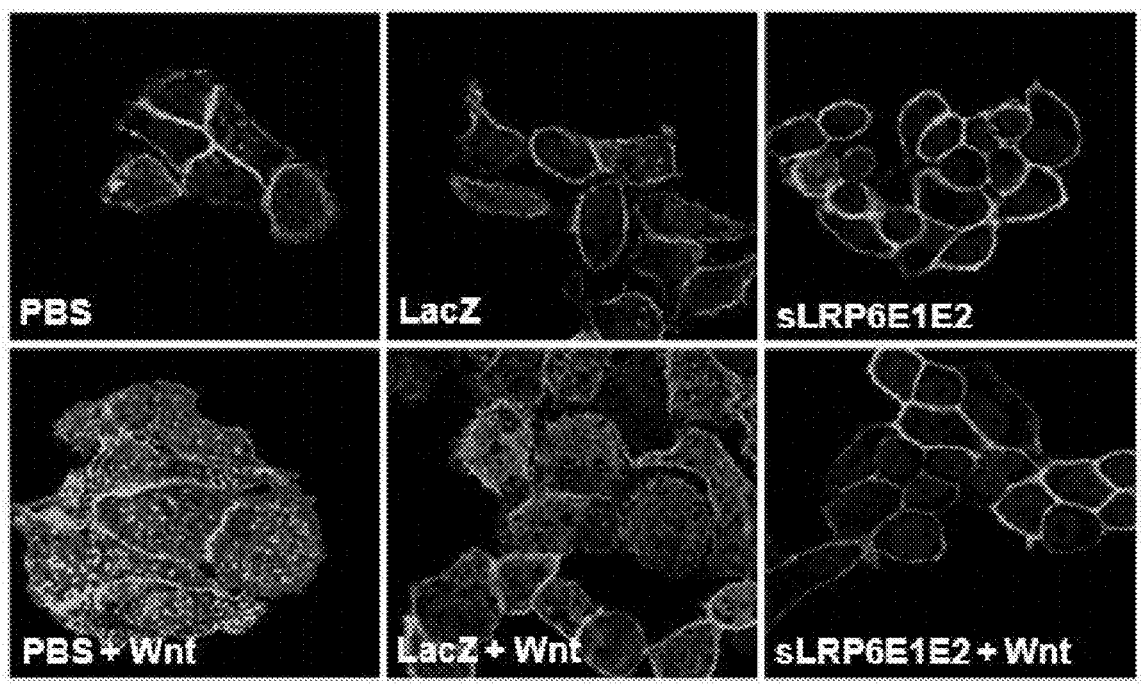
FIG. 2c shows H322 cells transduced with dE1-k35/LacZ or dE1-k35/sLRP6E1E2 (50 MOI) with or without Wnt3a and labeled with anti-β-catenin. Original magnification, ×630.

To evaluate the effect of sLRP6E1E2 on β-catenin localization, immune fluorescence staining was performed in H322 cells treated with PBS or transduced with dE1-k35/LacZ or dE1-k35/sLRP6E1E2. In the absence of Wnt3a, β-catenin staining was restricted primarily to cell-cell contact sites in all groups. Upon Wnt3a stimulation, control cells (PBS and dE1-k35/LacZ) showed reduced β-catenin localization at the plasma membrane, especially at cell-cell junctions, and increased β-catenin levels in the cytosol and nucleus. In contrast, dE1-k35/sLRP6E1E2-transduced cells showed lower levels of cytosolic β-catenin, and higher levels of membrane-associated β-catenin (FIG. 2c). Results of these functional studies demonstrate that interactions between sLRP6E1E2 and Wnt may be sufficient to block Wnt signaling.

Decoy Wnt Receptor sLRP6E1E2 Inhibits Lung Cancer Cell Proliferation

Figure 3A:
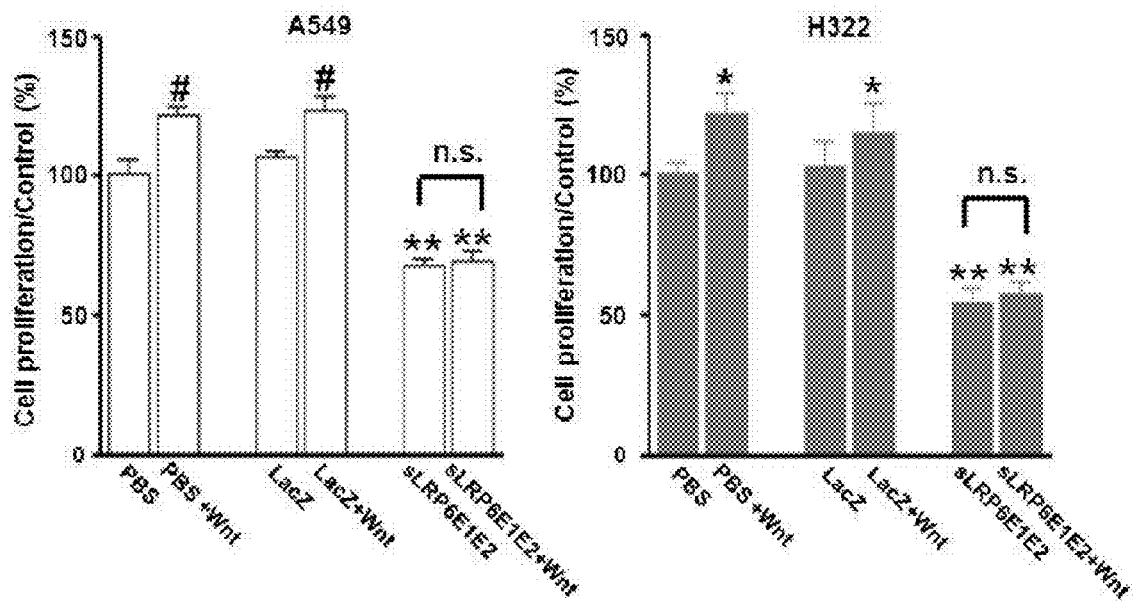
FIG. 3a shows A549 and H322 cells transduced with dE1-k35/LacZ or dE1-k35/sLRP6E1E2 (20 MOI). The next day, these cells were incubated with or without Wnt3a (100 ng/ml). After 3 days, cell proliferation was assessed by the MTT assay (mean±SEM). *$P<0.05$, #$P<0.01$ versus untreated control for each group; **$P<0.001$ versus dE1-k35/LacZ-transduced or PBS-treated cells. n.s.=not significant.

The Wnt pathway regulates a wide range of cellular functions including proliferation (25). To test the effects of sLRP6E1E2 on proliferation of A549 and H322 cells in vitro, cells were treated with PBS or transduced with dE1-k35/LacZ or dE1-k35/sLRP6E1E2. At 72 hr after transduction with dE1-k35/sLRP6E1E2 (20 MOI), cell proliferation was reduced by 39% in A549 cells and 51% in H322 cells compared with dE1-k35/LacZ-transduced controls. Wnt3a stimulation increased proliferation approximately 10-20% in control cells, but had no apparent effect on dE1-k35/sLRP6E1E2-transduced cells. Proliferation was 54% lower in A549 cells and 61% lower in H322 dE1-k35/sLRP6E1E2-transduced cells than dE1-k35/LacZ-transduced cells ($P<0.001$; FIG. 3a).

Figure 3B:
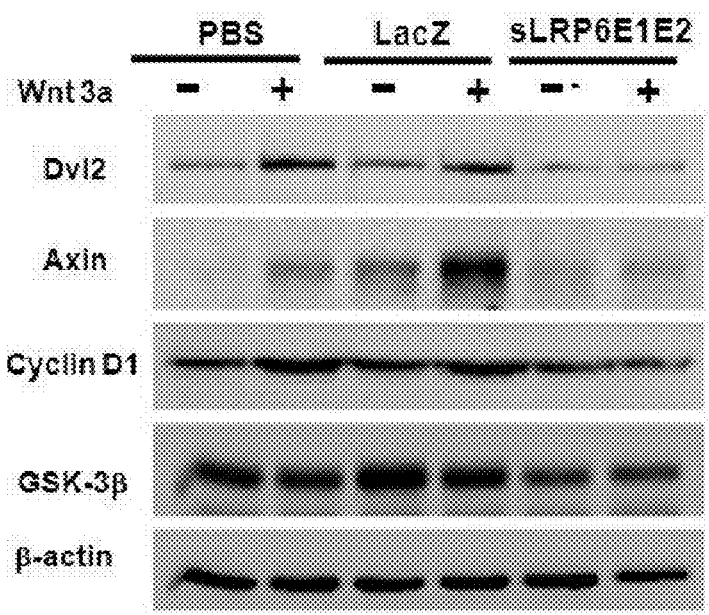
FIG. 3b represents the result of western blot analysis for A549 cells treated as indicated above (FIG. 3a) using antibodies specific to Dvl2, Axin, Cyclin D1, or GSK-3β.

To characterize signaling pathways involved in the antiproliferative action of sLRP6E1E2, we examined its effects on canonical Wnt signaling. As shown in FIG. 3B, Dvl2 and Axin protein levels in control cells (PBS and dE1-k35/LacZ) were increased by Wnt3a, but were apparently unaltered by Wnt3a in dE1-k35/sLRP6E1E2-transduced cells. Similarly, cyclin D1 expression was slightly increased in control cells following Wnt3a stimulation, but slightly decreased in dE1-k35/sLRP6E1E2-transduced cells. GSK3β levels also appeared slightly decreased after Wnt3a treatment.

Figure 3C:
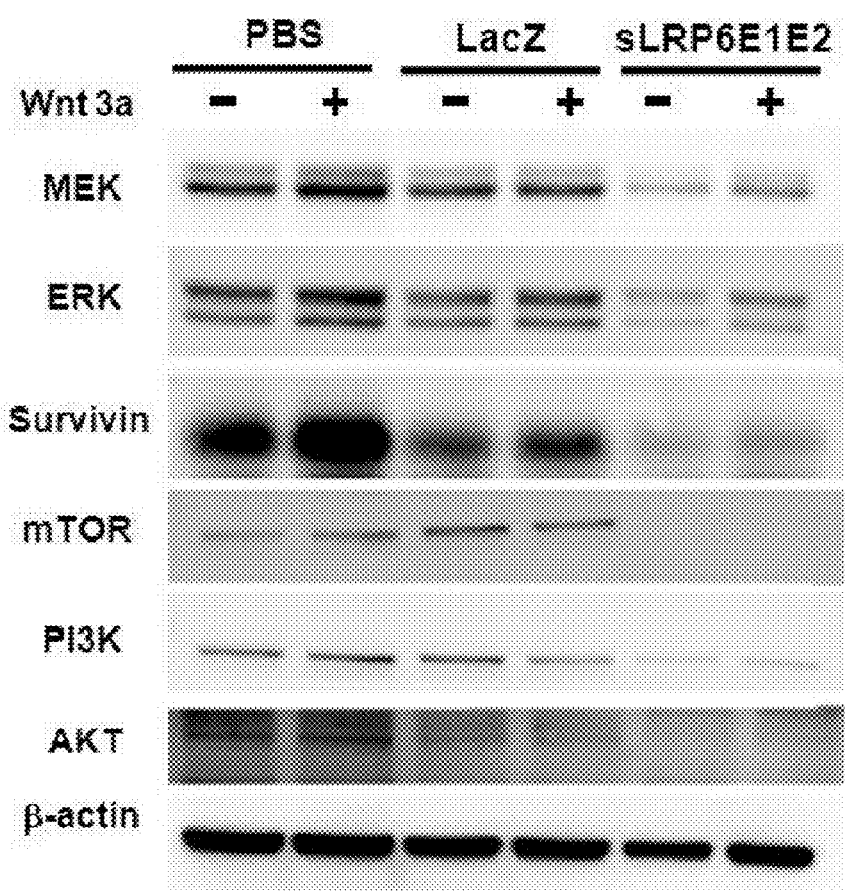
FIG. 3c represents the result of western blot analysis for MEK, ERK, Survivin, mTOR, PI3K, and Akt in H460 cells treated 50 MOI as indicated above (FIG. 3a).

Wnt plays a fundamental role in proliferation by activating ERK and PI3K-Akt pathways (26). We therefore investigated whether sLRP6E1E2 can downregulate these pathways in H460 cells. We found that basal levels of MEK, ERK1/2, and survivin were lower in dE1-k35/sLRP6E1E2-transduced cells than in control cells (FIG. 3c). These proteins were upregulated by Wnt3a treatment, but levels were still considerably lower in dE1-k35/sLRP6E1E2-transduced cells than in the controls. Expression of mTOR, PI3K, and Akt was not affected by Wnt3a stimulation, and was lower in dE1-k35/sLRP6E1E2-transduced cells than controls. Taken together, these results suggest that sLRP6E1E2 exerts antiproliferative actions by inhibiting Wnt signaling via MEK-ERK and PI3K-Akt pathways.

Decoy Wnt Receptor sLRP6E1E2 Induces Apoptosis

Figure 4A:
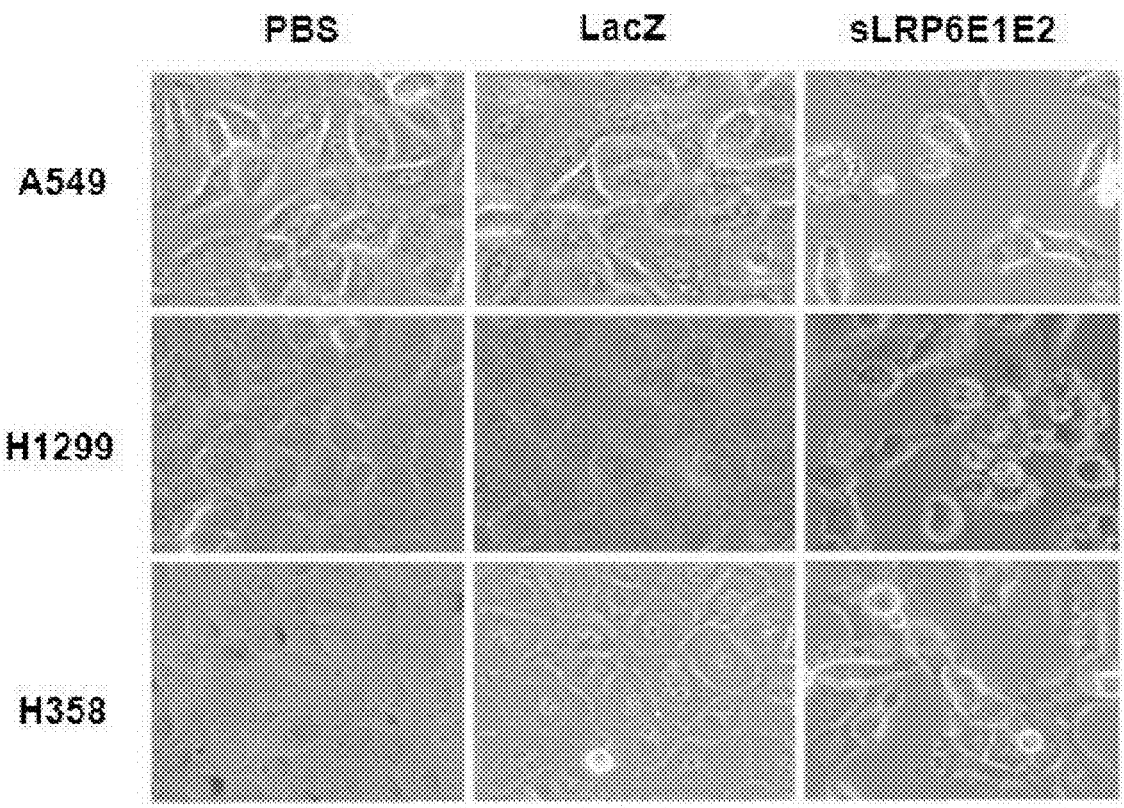
FIG. 4a shows photographs taken 72 hr after cells were transduced with dE1-k35/LacZ or dE1-k35/sLRP6E1E2 at (20 MOI). Original magnification, ×200.
Figure 4B:
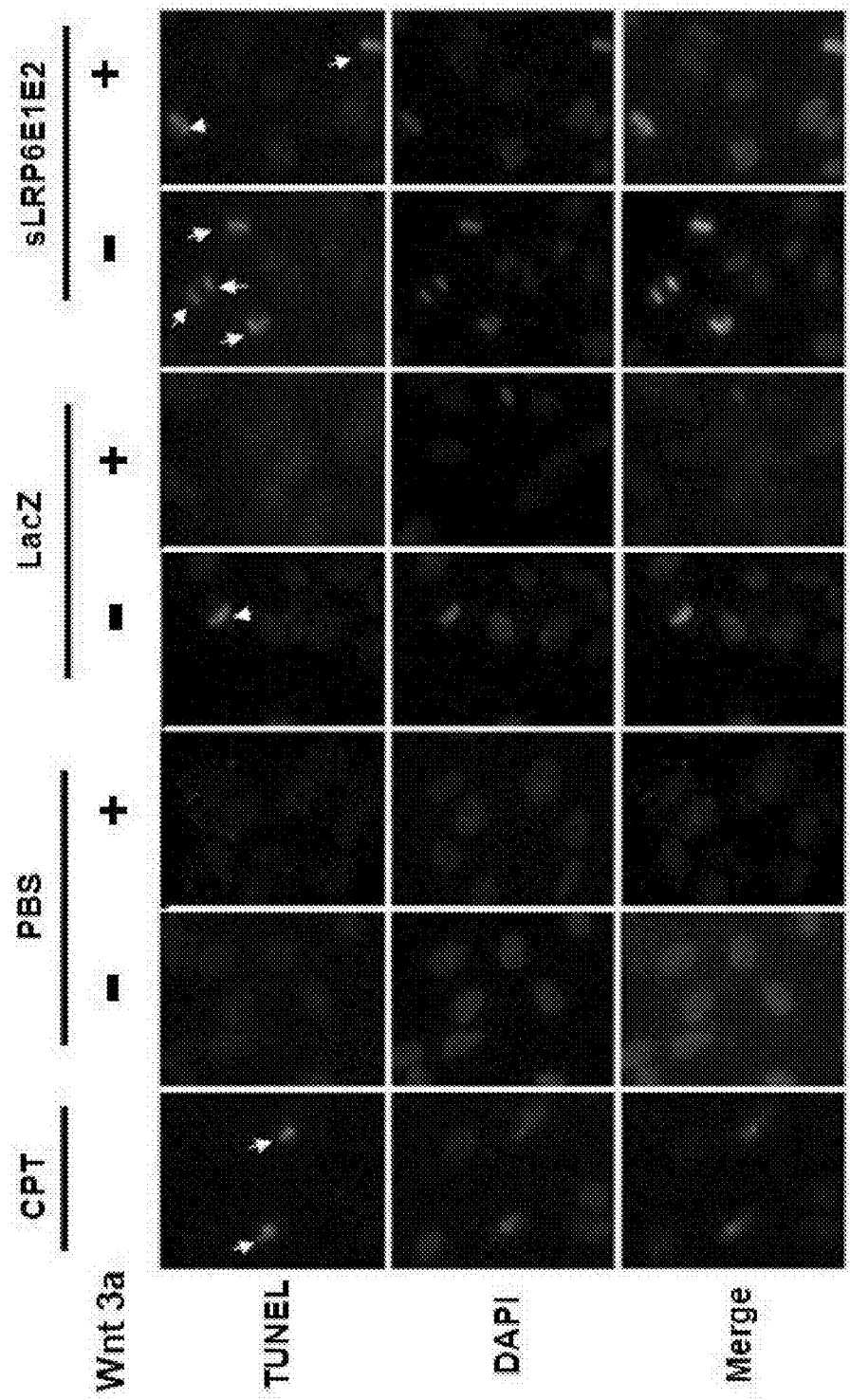
FIG. 4b represents detection of sLRP6E1E2-induced apoptosis by TUNEL staining. Original magnification, ×400.
Figure 4C:
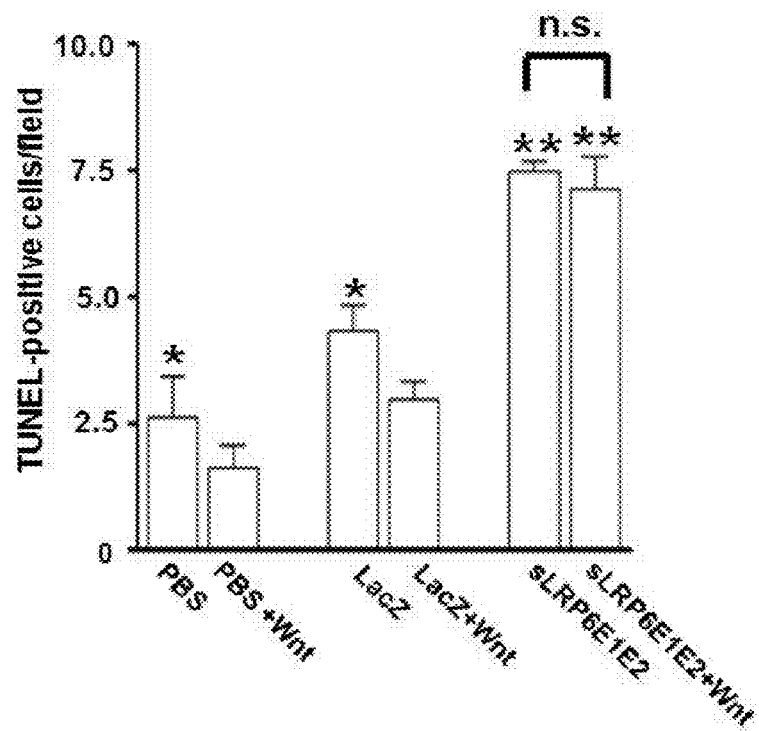
FIG. 4c indicates total number of TUNEL-positive cells per fields (mean±SEM). *P<0.05 versus PBS or dE1-k35/LacZ treated with Wnt3a; **P<0.001 versus PBS-treated or dE1-k35/LacZ-transduced controls. n.s.=not significant.

Wnt signaling can prevent apoptosis and promote cellular proliferation and survival (27). To characterize the molecular mechanisms by which sLRP6E1E2 inhibits non-small cell lung cancer proliferation, we evaluated the effects of sLRP6E1E2 on apoptosis. At 3 days after dE1-k35/sLRP6E1E2 transduction, we observed that A549, H1299, and H358 cells gradually detached from the culture dish and became rounder and smaller than attached cells (FIG. 4a), suggesting that sLRP6E1E2 induced apoptosis. Evidence of apoptosis was sought by looking for nuclear apoptotic bodies (data not shown), and then assessed using the TUNEL assay to detect internucleosomal DNA fragmentation (28). As shown in FIG. 4b, more TUNEL-positive cells were observed among dE1-k35/sLRP6E1E2-transduced cells than among control cells in the presence or absence of Wnt3a. Quantitation of TUNEL staining revealed that the rate of apoptosis was approximately 1.9-fold higher (without Wnt3a) and 2.8-fold higher (with Wnt3a) in dE1-k35/sLRP6E1E2-transduced cells than in dE1-k35/LacZ-transduced controls (P<0.001) (FIG. 4c).

Figure 4D:
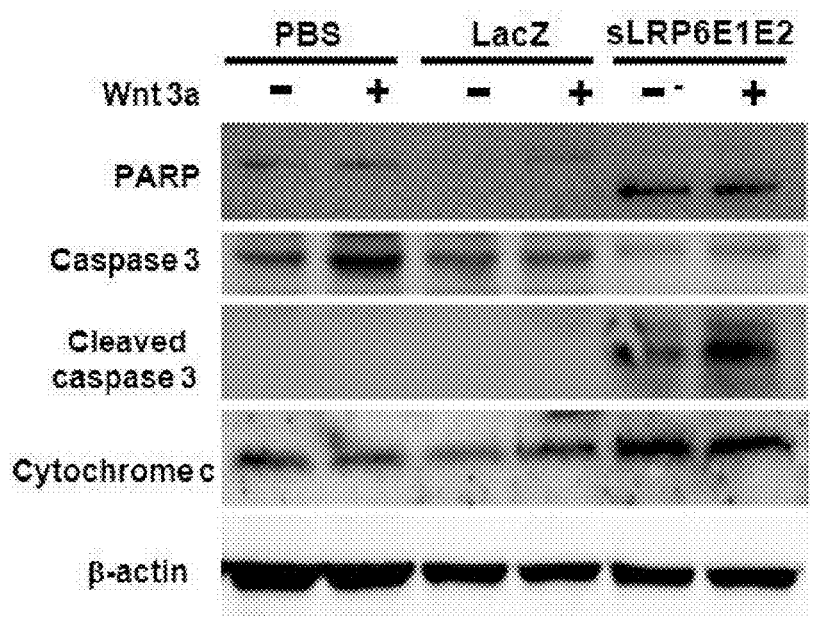
FIG. 4d represents the result of western blot analysis of sLRP6E1E2-mediated apoptosis. H460 cells were transduced with dE1-k35/LacZ or dE1-k35/sLRP6E1E2 (20 MOI). The western blot using specific antibodies against uncleaved PARP, cleaved PARP, pro-caspase-3, cleaved caspase-3, and cytochrome c.
Figure 4E:
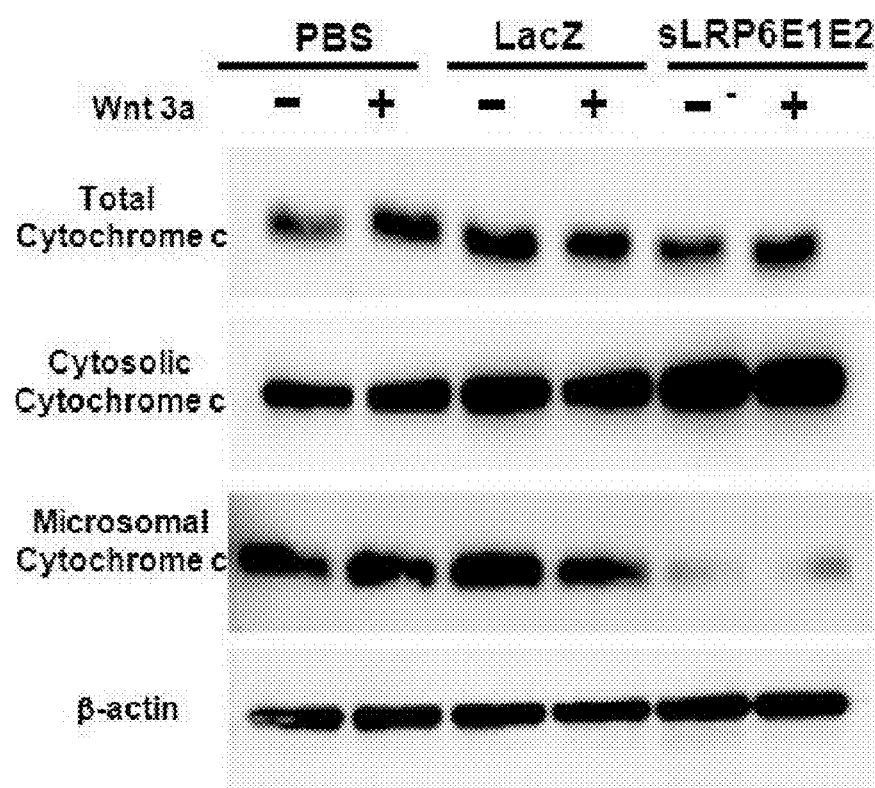
FIG. 4e represents subcellular localization of cytochrome c in H460 cells treated as indicated above (FIG. 4d), determined by western blot analysis of cytosolic and microsomal fractions.
Figure 4F:
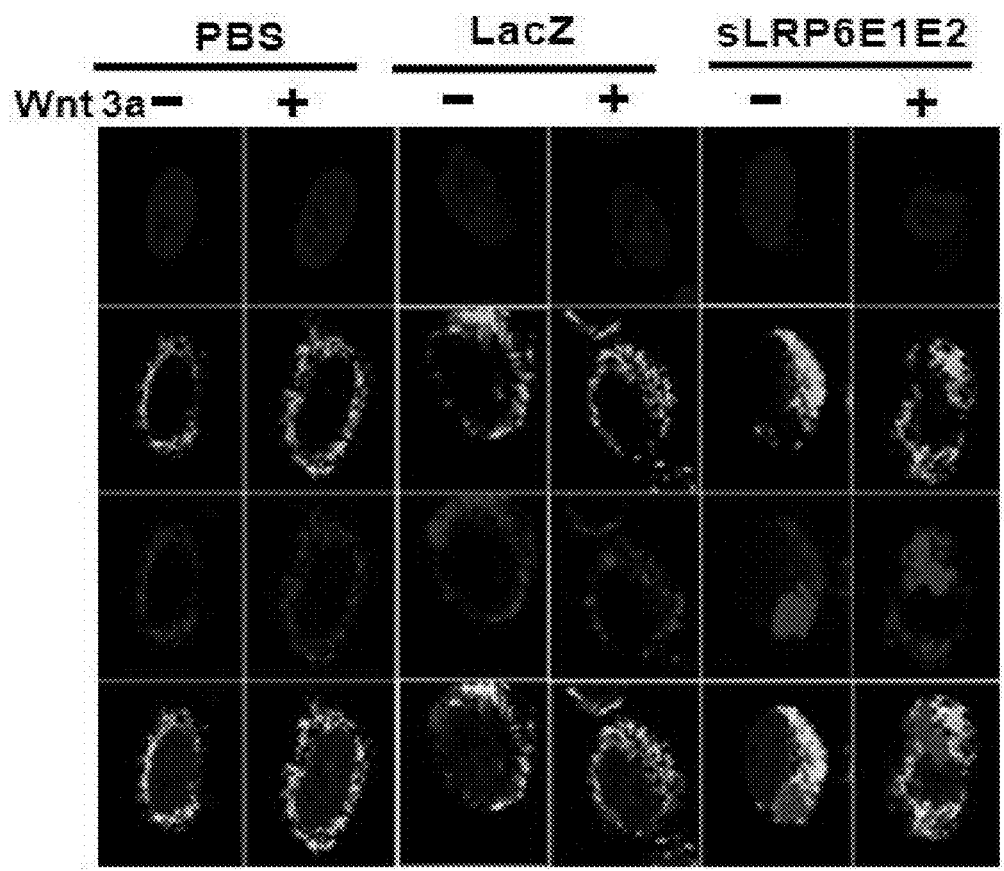
FIG. 4f shows represents laser fluorescence confocal microscopy image of A549 cells treated as indicated above (FIG. 4d). Cells were stained with anti-cytochrome c (green) and MitoTracker (red).

We next evaluated regulators of apoptosis, of which the caspase family and cytochrome c are the best characterized. In the absence and presence of Wnt3a, full-length 116-kDa PARP protein was reduced and 85-kDa cleavage fragments were increased in dE1-k35/sLRP6E1E2-transduced cells (FIG. 4d). Levels of the cleaved (active) form of caspase-3 were also markedly increased by sLRP6E1E2. As shown in FIG. 4e, dE1-k35/sLRP6E1E2-transduced cells also showed increased cytosolic cytochrome c and decreased microsomal cytochrome c. Stimulation with Wnt3a produced similar effects. To further investigate cytochrome c localization, immunofluorescence was performed. PBS-treated and dE1-k35/LacZ-transduced cells displayed punctuate cytoplasmic staining of cytochrome c, consistent with mitochondrial localization. In contrast, cells expressing sLRP6E1E2 exhibited mostly diffuse cytoplasmic cytochrome c staining, consistent with translocation from mitochondria to cytoplasm (FIG. 4f).

Decoy Wnt Receptor sLRP6E1E2 Inhibits Tumor Xenograft Growth

We next evaluated the ability of sLRP6E1E2 to inhibit tumor growth in a mouse xenograft model. Tumors were generated by subcutaneous injection of H460 cells into the abdominal region of nude mice. When tumors reached a mean size of 80-100 mm$^3$, they were injected with PBS, dE1-k35, RdB-k35, dE1-k35/sLRP6E1E2, or RdB-k35/sLRP6E1E2 on days 1, 3, and 5. FIG. 5a shows that the volume of tumors injected with sLRP6E1E2-expressing vectors was significantly lower than that of corresponding controls. After 25 days, tumors treated with PBS reached a mean volume of 3883.1±418.08 mm$^3$, and tumors treated with dE1-k35 and RdB-k35 reached 3388.1±226.9 mm$^3$ and 1991±311.8 mm$^3$, respectively. In contrast, tumor growth was strongly suppressed in mice injected with dE1-k35/sLRP6E1E2 (1645.3±353.6 mm$^3$; P<0.05 compared with PBS or dE1-k35 groups) or RdB-k35/sLRP6E1E2 (923.3±180.4 mm$^3$; P<0.01 compared with PBS or RdB-k35 groups).

Figure 5B:
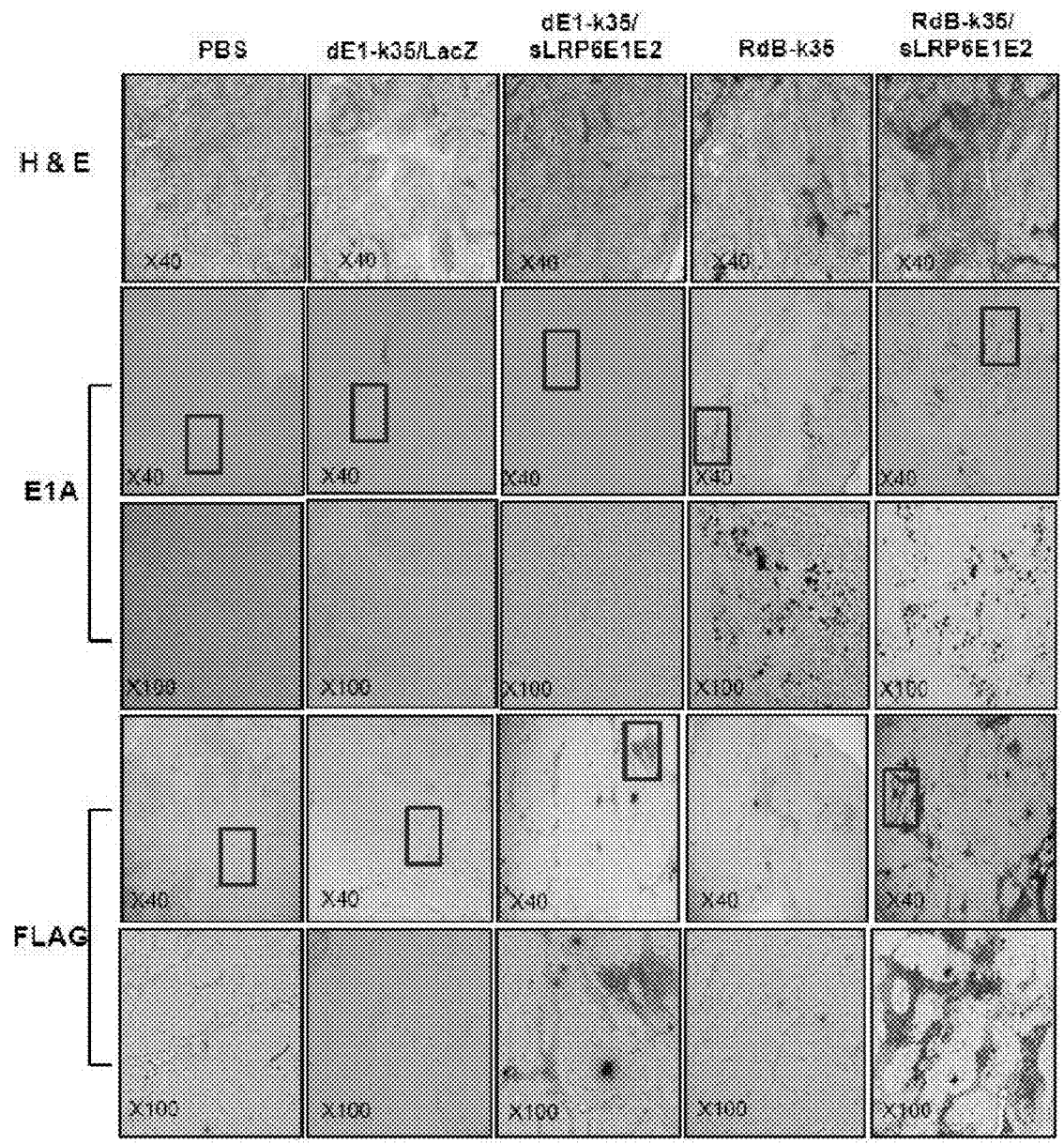
FIG. 5b shows tumor sections from each group were immunostained against E1A or FLAG (original magnification, ×40 and ×100).

To evaluate the biological effects of sLRP6E1E2 in tumor tissue, tumors were harvested 3 days after the final adenovirus injection. Analysis of adenoviral E1A protein expression revealed that RdB-k35 and RdB-k35/sLRP6E1E2 had replicated and spread through the tumor (FIG. 5b, E1A). Immunohistochemical analysis of sLRP6E1E2 (FIG. 5b, FLAG) showed that its expression was more widespread in RdB-k35/sLRP6E1E2-treated tumors than in dE1-k35/sLRP6E1E2-treated tumors, indicating that the oncolytic adenovirus more efficiently expressed sLRP6E1E2 than the replication-incompetent adenovirus, contributing to its superior antitumor actions.

Figure 5C:
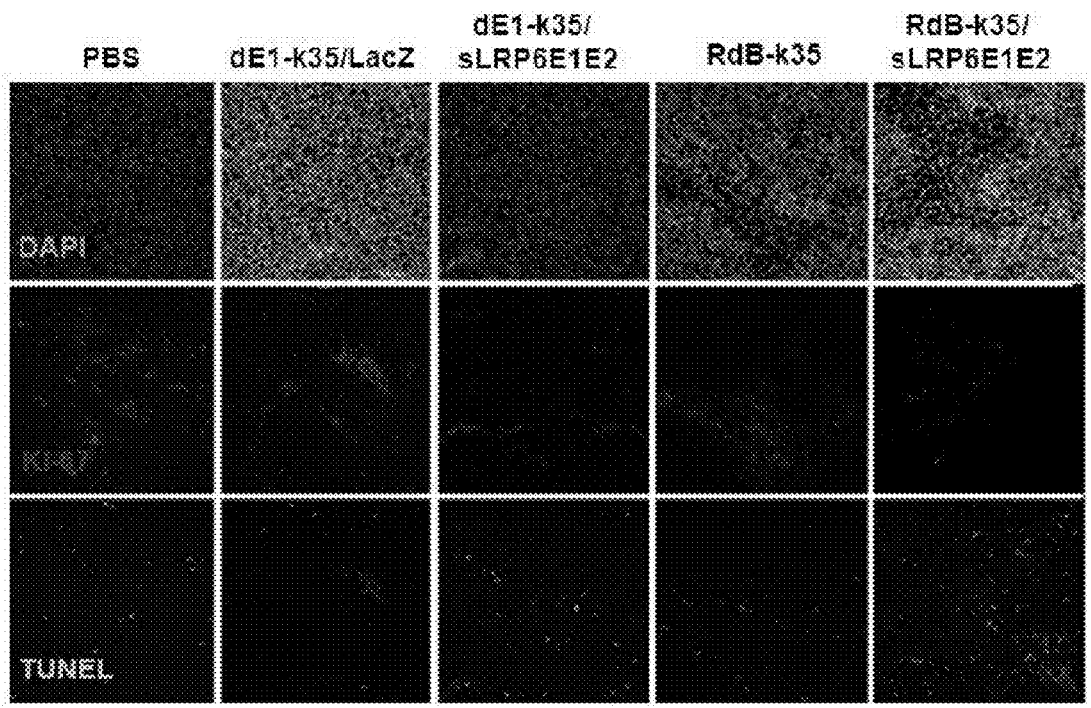
FIG. 5c shows images of tumor tissues from each group stained with DAPI (blue), anti-Ki67 (red), and TdT-mediated TUNEL (green). Original magnification: ×100.
Figure 5D:
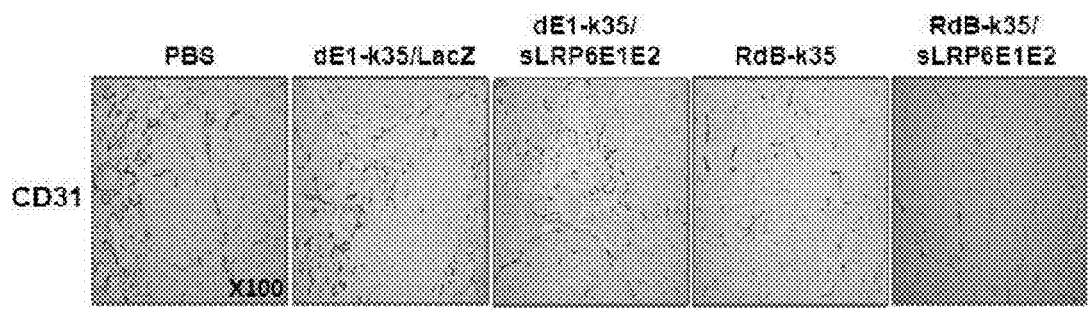
FIG. 5d shows blood vessels visualized by staining for CD31. Original magnification, ×100.
Figure 5E:
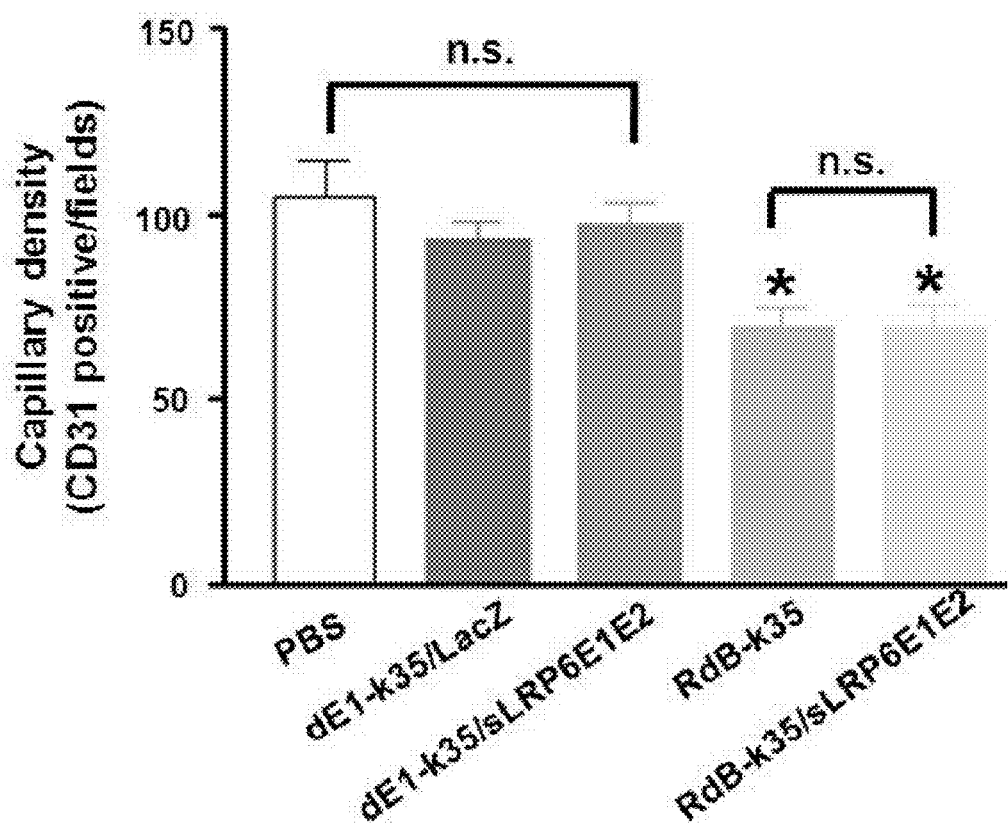
FIG. 5e indicates mean microvessel density for each treatment group (CD31 positive cells/field). Results are expressed as mean±SEM (each group, n=3 tumors). *P<0.05 versus PBS, dE1-k35, or dE1-k35/sLRP6E1E2. n.s.=not significant.

Anti-Proliferative and Apoptotic Effects of sLRP6E1E2-Expressing Vectors in H460 Xenografts To assess the effects of sLRP6E1E2 on tumor xenograft growth in mice, tumor samples were analyzed by Ki-67 immunostaining for proliferating cells and TUNEL staining for apoptotic cells. We found that Ki-67 expression was reduced and TUNEL-positive cells were increased in tumors treated with dE1-k35/sLRP6E1E2 or RdB-k35/sLRP6E1E2 compared with corresponding controls (FIG. 5c). We also detected more TUNEL-positive cells in RdB-k35/sLRP6E1E2-treated tumors than in dE1-k35/sLRP6E1E2-treated tumors, consistent with previous results. To determine whether the smaller sLRP6E1E2-treated tumors exhibited reduced neovascularization, microvessel density was assessed by CD31 staining Fewer endothelial cells and vessel structures was observed in tissues injected with E1-expressing oncolytic adenoviruses (RdB-k35 and RdB-k35/sLRP6E1E2) than PBS-treated tumors (P<0.05), whereas no significant decrease in vascular density was observed in tumors injected with dE1-k35 or dE1-k35/sLRP6E1E2 (FIGS. 5d & 5e). Further, vessel density in tumors injected with sLRP6E1E2-expressing adenoviruses did not differ from their corresponding controls, suggesting that the antitumor properties of sLRP6E1E2 were not mediated by anti-angiogenic effects.

Figure 5F:
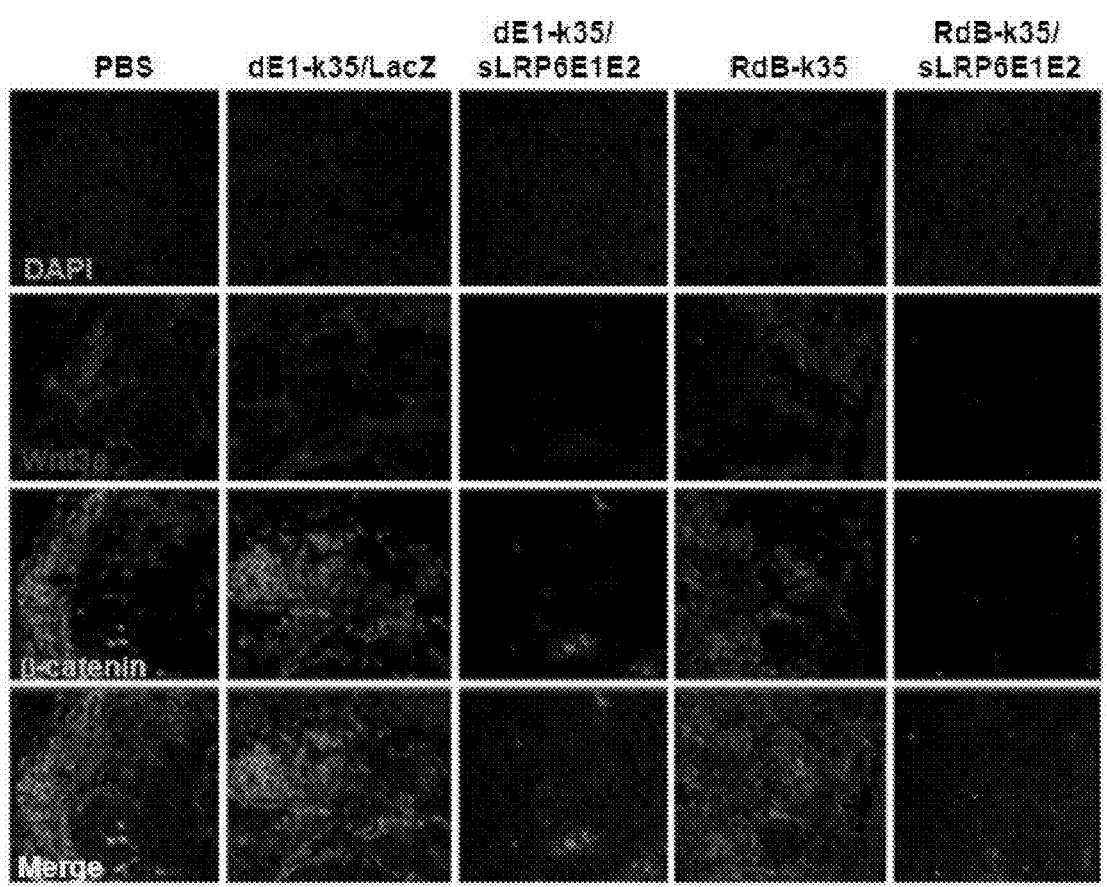
FIG. 5f shows images of cells stained with DAPI (blue), anti-Wnt3a (red), or anti-β-catenin (green). Original magnification: ×100.

To further investigate the role of Wnt signaling in the antitumor actions of sLRP6E1E2-expressing adenoviruses, Wnt and β-catenin localization in tumor tissue was evaluated. High endogenous expression of β-catenin and Wnt was observed in tumor tissues treated with PBS or control vectors (dE1-k35 and RdB-k35) (FIG. 5F), but was significantly reduced by sLRP6E1E2-expressing vectors, suggesting that blockade of Wnt signaling in tumor cells was an important contributor to slower tumor growth.

Wnt Treatment Results Altered Cell Morphology and Induces EMT in Tumor Cells

Figure 6A:
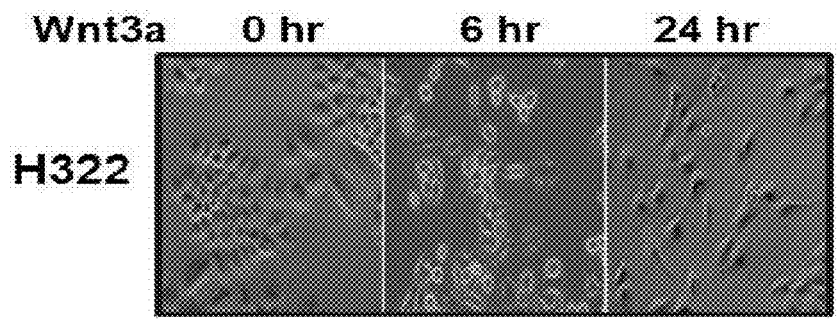
FIG. 6a represents morphology changes of H322 cells by treatment of Wnt3a (100 ng/ml) for the indicated times. Original magnification, ×200.
Figure 6B:
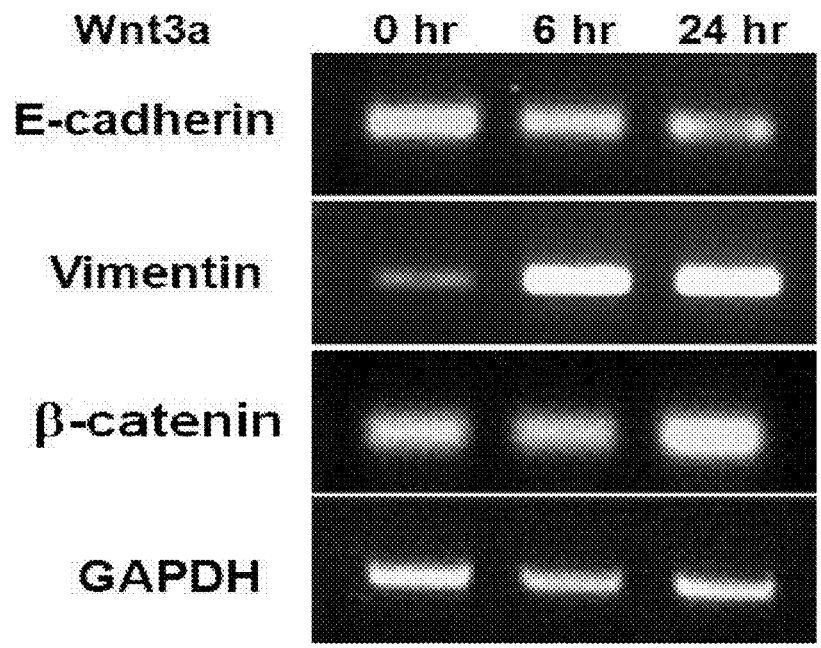
FIG. 6b shows E-cadherin, Vimentin, and β-catenin mRNA levels in H322 cells after Wnt3a treatment.
Figure 6C:
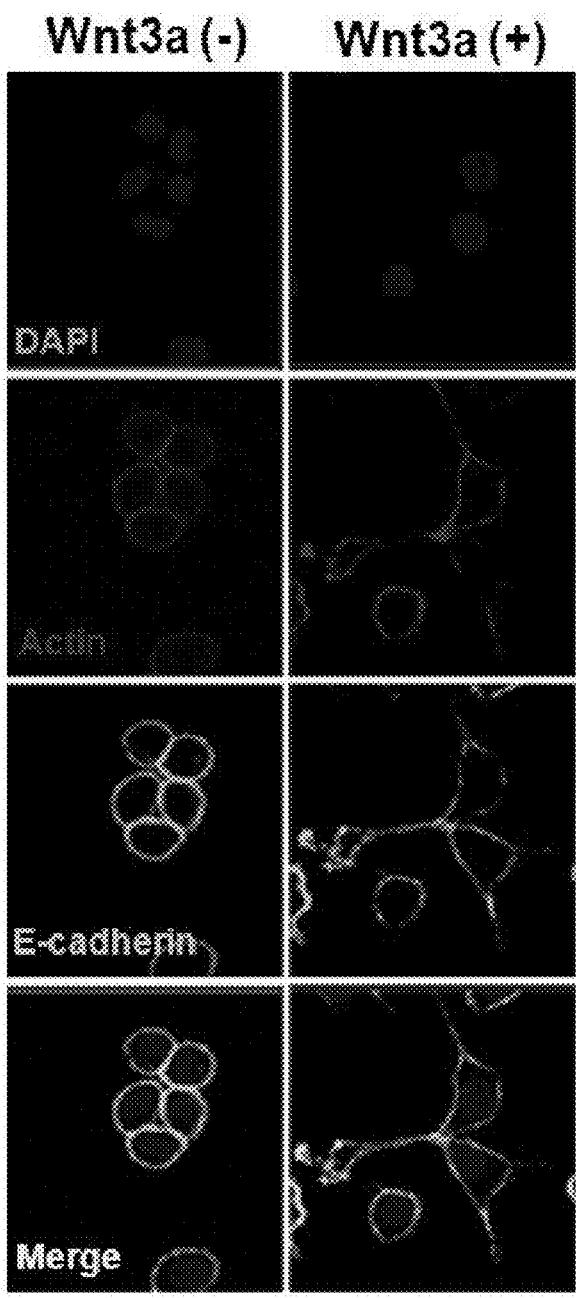
FIG. 6c shows images of H322 cells stained with DAPI (blue), TRITC-labeled phalloidin (red), or anti E-cadherin (green) after 24 incubation with or without Wnt3a (100 ng/ml). Original magnification, ×630.

EMT is an important process in tumor development, and the Wnt/β-catenin signal pathway may play an important role in this process. Therefore, we investigated whether Wnt3a could induce EMT in H322 cells. We found that cells became elongated and spindle-shaped 1 day after Wnt3a treatment, resembling the morphology of mesenchymal cells (FIG. 6a). We also observed increased expression of mesenchymal markers Vimentin and β-catenin with a concomitant decrease in epithelial marker E-cadherin (FIG. 6b) Immunofluorescence staining revealed that cytokeratin and E-cadherin levels were dramatically reduced in cell-cell contacts after Wnt3a treatment (FIG. 6c).

sLRP6E1E2 Modulates EMT-Related Marker Expression and MMP-2/MMP-9 Activity.

Figure 7A:
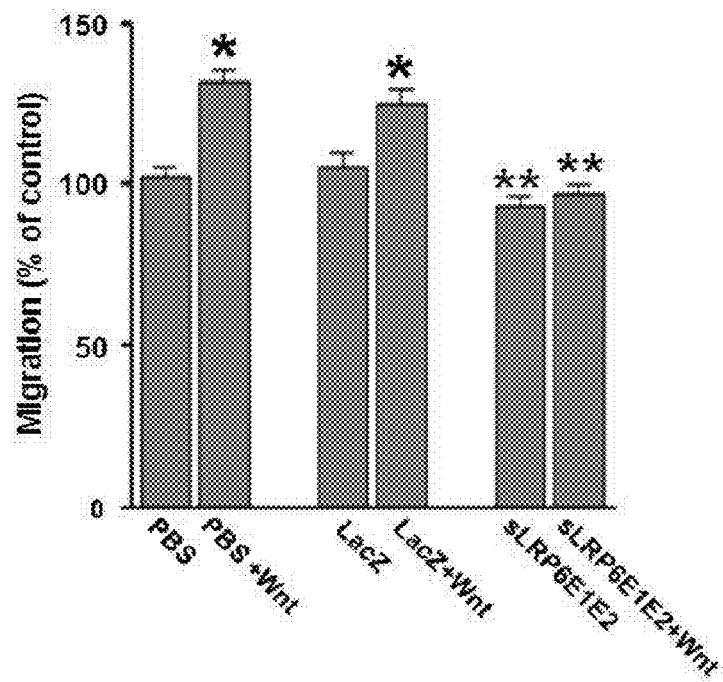
Figure 7B:
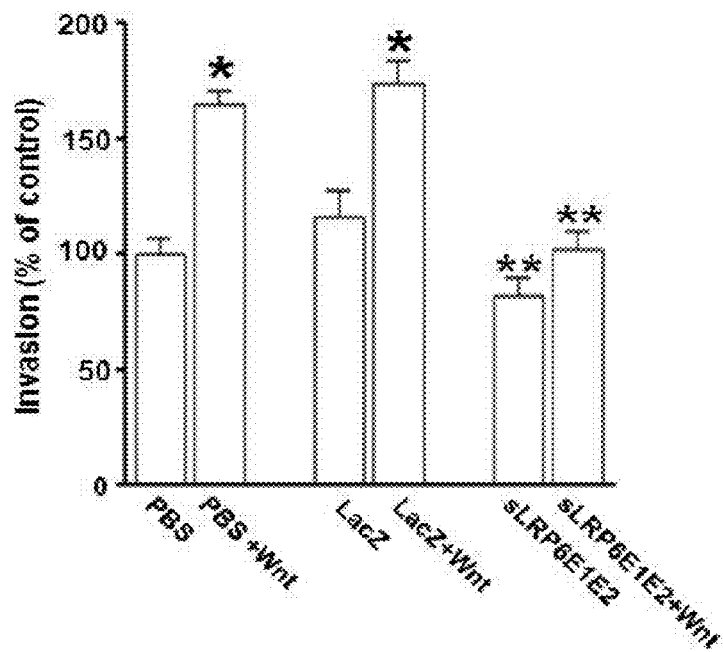
Figure 7C:
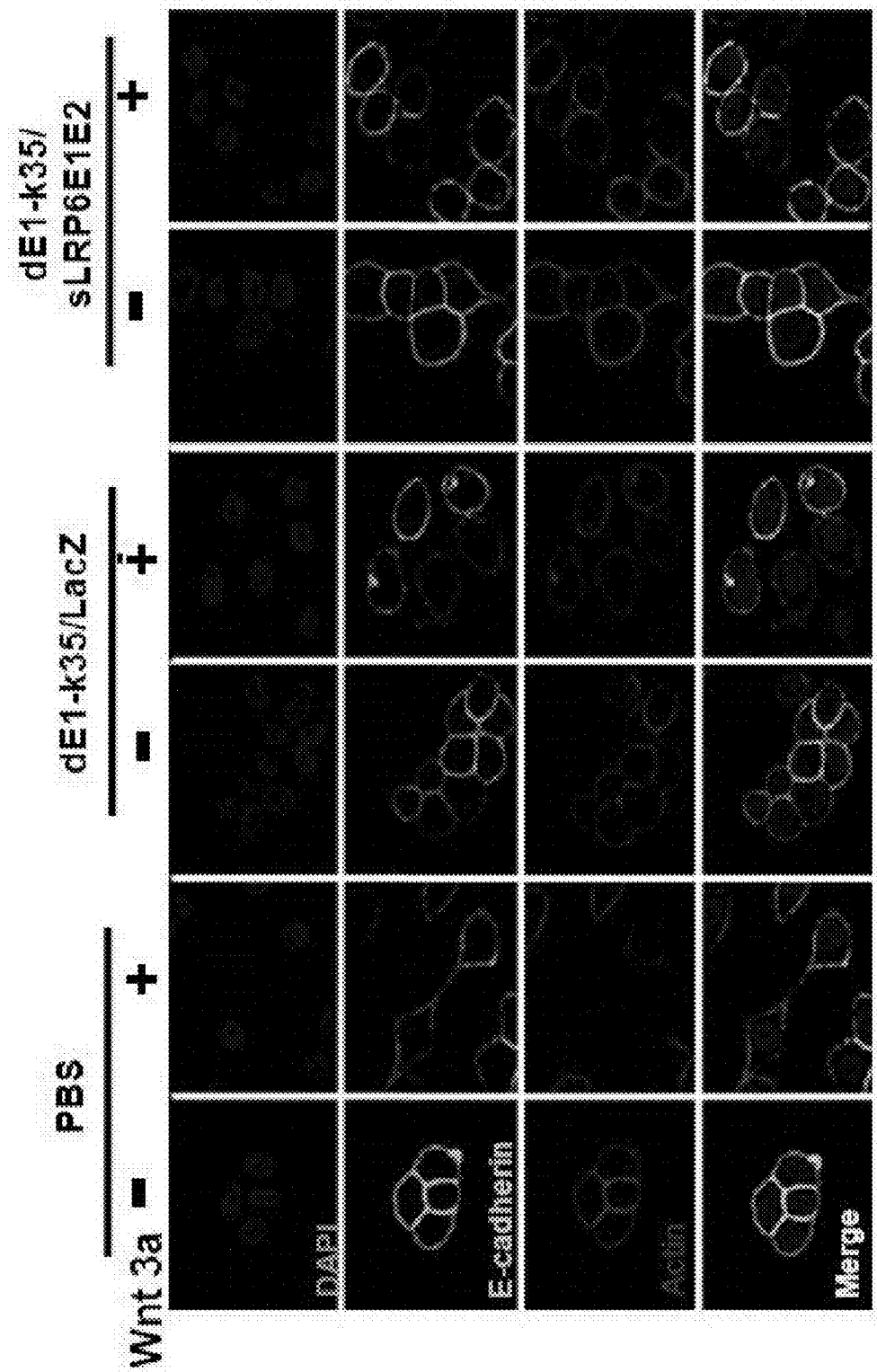
FIG. 7c shows expression of EMT markers in H322 cells after 24 hr treatment with PBS, dE1-k35/LacZ, or dE1-k35/sLRP6E1E2 in the presence and absence of Wnt3a (100 ng/ml). Cells were stained with DAPI (blue), TRITC-labeled phalloidin (red), or anti E-cadherin (green). Original magnification, ×630.

Acquisition of migratory properties by cancer cells is important for metastatic tumor cell spread (29). Because increasing Wnt3a appeared to enhance motility and invasiveness, we asked whether interfering with the Wnt signaling pathway by expressing sLRP6E1E2 would inhibit in vitro motility and invasion. We examined the effect of sLRP6E1E2 on A549 cells using transwell motility and matrigel invasion assays. We collected conditioned medium from PBS-treated, dE1-k35/LacZ-transduced, and dE1-k35/sLRP6E1E2-transduced cells after treatment with or without Wnt3a. Conditioned medium from dE1-k35/sLRP6E1E2-transduced cells inhibited migration by 12.4% (without Wnt3a) and 23.8% (with Wnt3a) compared with conditioned medium from dE1-k35/LacZ-transduced cells (P<0.001) (FIG. 7a). Similarly, conditioned medium from dE1-k35/sLRP6E1E2-transduced cells inhibited invasion by 34.2% (without Wnt3a) and 56.2% (with Wnt3a) compared with conditioned medium from dE1-k35/LacZ-transduced cells (FIG. 7b). E-cadherin expression and actin filaments were also decreased by Wnt3a, but were increased in dE1-k35/sLRP6E1E2-transduced cells compared with controls with or without Wnt3a treatment (FIG. 7c).

Figure 7D:
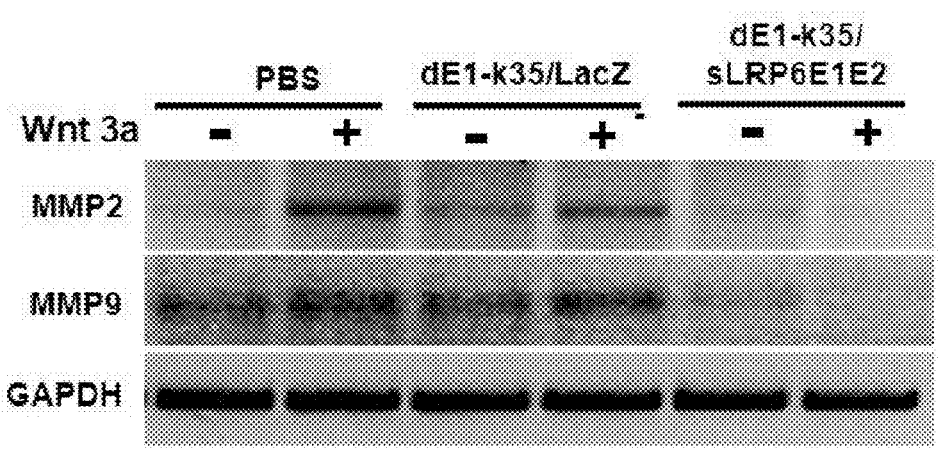
FIG. 7d shows expression of MMP-2 and MMP-9 mRNA levels in A549 cells treated as indicated above (FIG. 3a), analyzed by semiquantitative RT-PCR.

Invasion and metastasis of malignantly transformed cells involve degradation of extracellular matrix by matrix metalloproteinases (MMPs). We therefore examined the effect of sLRP6E1E2 on expression of MMP-2 and MMP-9, which play a critical role in angiogenesis, tumor growth, and metastasis. As shown in FIG. 7d, Wnt3a stimulation upregulated MMP-2 and MMP-9 in PBS-treated and dE1-k35/LacZ-transduced A549 cells, but dE1-k35/sLRP6E1E2-transduced cells showed low MMP-2 and MMP-9 expression with or without Wnt3a treatment. Taken together, these findings suggest that sLRP6E1E2 affected multiple Wnt-related pathways in human non-small cell lung cancer cell lines, leading to reduced cellular invasiveness.

REFERENCES

1. Burstein H J, Gelber S, Guadagnoli E, Weeks J C. Use of alternative medicine by women with early-stage breast cancer. *N Engl J Med* 340:1733-9 (1999).
2. Broxterman H J, Georgopapadakou N H. Anticancer therapeutics: a surge of new developments increasingly target tumor and stroma. *Drug Resist Updat* 10:182-93 (2007).
3. Liu J R, Opipari A W, Tan L, et al. Dysfunctional apoptosome activation in ovarian cancer: implications for chemoresistance. *Cancer Res* 62:924-31 (2002).
4. Fukui T, Otani S, Hataishi R, et al. Successful rechallenge with erlotinib in a patient with EGFR-mutant lung adenocarcinoma who developed gefitinib-related interstitial lung disease. *Cancer Chemother Pharmacol* 65:803-6 (2010).
5. Lynch T J, Bell D W, Sordella R, et al. Activating mutations in the epidermal growth factor receptor underlying responsiveness of non-small-cell lung cancer to gefitinib. *N Engl J Med* 350:2129-39 (2004).
6. Nishio M, Koshikawa T, Kuroishi T, et al. Prognostic significance of abnormal p53 accumulation in primary, resected non-small-cell lung cancers. *J Clin Oncol* 14:497-502 (1996).
7. Nishio M, Koshikawa T, Yatabe Y, et al. Prognostic significance of cyclin D1 and retinoblastoma expression in combination with p53 abnormalities in primary, resected non-small cell lung cancers. *Clin Cancer Res* 3:1051-8 (1997).
8. Mitsudomi T, Kosaka T, Endoh H, et al. Mutations of the epidermal growth factor receptor gene predict prolonged survival after gefitinib treatment in patients with non-small-cell lung cancer with postoperative recurrence. *J Clin Oncol* 23:2513-20 (2005).
9. Nusse R, Theunissen H, Wagenaar E, et al. The Wnt-1 (int-1) oncogene promoter and its mechanism of activation by insertion of proviral DNA of the mouse mammary tumor virus. *Mol Cell Biol* 10:4170-9 (1990).
10. Beachy P A, Karhadkar S S, Berman D M. Tissue repair and stem cell renewal in carcinogenesis. *Nature* 432:324-31 (2004).
11. Holcombe R F, Marsh J L, Waterman M L, Lin F, Milovanovic T, Truong T. Expression of Wnt ligands and Frizzled receptors in colonic mucosa and in colon carcinoma. *Mol Pathol* 55:220-6 (2002).
12. DeAlmeida V I, Miao L, Ernst J A, Koeppen H, Polakis P, Rubinfeld B. The soluble wnt receptor Frizzled8CRD-hFc inhibits the growth of teratocarcinomas in vivo. *Cancer Res* 67:5371-9 (2007).
13. Li Y, Lu W, He X, Schwartz A L, Bu G. LRP6 expression promotes cancer cell proliferation and tumorigenesis by altering beta-catenin subcellular distribution. *Oncogene* 23:9129-35 (2004).
14. Liu C C, Pearson C, Bu G. Cooperative folding and ligand-binding properties of LRP6 beta-propeller domains. *J Biol Chem* 284:15299-307 (2009).
15. He X, Semenov M, Tamai K, Zeng X. LDL receptor-related proteins 5 and 6 in Wnt/beta-catenin signaling: arrows point the way. *Development* 131:1663-1677 (2004).
16. Zhang Y, Wang Y, Li X, et al. The LRP5 high-bone-mass G171V mutation disrupts LRP5 interaction with Mesd. *Mol Cell Biol* 24:4677-84(2004).
17. Forrester W C. The Ror receptor tyrosine kinase family. *Cell Mol Life Sci* 59:83-96(2002).
18. Signorello L B, Cohen S S, Bosetti C, et al. Female survivors of childhood cancer: preterm birth and low birth weight among their children. *J Natl Cancer Inst* 98:1453-61(2006).
19. Yoo J Y, Kim J H, Kwon Y G, et al. VEGF-specific short hairpin RNA-expressing oncolytic adenovirus elicits potent inhibition of angiogenesis and tumor growth. *Mol Ther* 15:295-302(2007).
20. Yoon A R, Kim J H, Lee Y S, et al. Markedly enhanced cytolysis by E1B-19kD-deleted oncolytic adenovirus in combination with cisplatin. *Hum Gene Ther* 17:379-90 (2006).
21. Kim J, Kim J H, Choi K J, Kim P H, Yun C O. E1A- and E1B-Double mutant replicating adenovirus elicits enhanced oncolytic and antitumor effects. *Hum Gene Ther* 18:773-86(2007).
22. Yun C O, Kim E, Koo T, Kim H, Lee Y S, Kim J H. ADP-overexpressing adenovirus elicits enhanced cytopathic effect by induction of apoptosis. *Cancer Gene Ther* 12:61-71(2005).
23. Yoo J Y, Kim J H, Kim J, et al. Short hairpin RNA-expressing oncolytic adenovirus-mediated inhibition of IL-8: effects on antiangiogenesis and tumor growth inhibition. *Gene Ther* 15:635-51(2008).
24. Korinek V, Barker N, Morin P J, et al. Constitutive transcriptional activation by a beta-catenin-Tcf complex in APC-/- colon carcinoma. *Science* 275:1784-1787 (1997).
25. Yun M S, Kim S E, Jeon S H, Lee J S, Choi K Y. Both ERK and Wnt/beta-catenin pathways are involved in Wnt3a-induced proliferation. *J Cell Sci* 118:313-22 (2005).
26. Kim S E, Lee W J, Choi K Y. The PI3 kinase-Akt pathway mediates Wnt3a-induced proliferation. *Cell Signal* 19:511-8(2007).
27. Grotewold L, Ruther U. The Wnt antagonist Dickkopf-1 is regulated by Bmp signaling and c-Jun and modulates programmed cell death. *EMBO J* 21:966-75(2002).
28. Yang L, Mashima T, Sato S, et al. Predominant suppression of apoptosome by inhibitor of apoptosis protein in non-small cell lung cancer H460 cells: therapeutic effect of a novel polyarginine-conjugated Smac peptide. *Cancer Res* 63:831-7(2003).
29. Gupta G P, Massague J. Cancer metastasis: building a framework. *Cell* 127:679-95(2006).
30. Uematsu K, He B, You L, Xu Z, McCormick F, Jablons D M. Activation of the Wnt pathway in non small cell lung cancer: evidence of dishevelled overexpression. *Oncogene* 22:7218-21(2003).

31. He B, You L, Uematsu K, et al. A monoclonal antibody against Wnt-1 induces apoptosis in human cancer cells. *Neoplasia* 6:7-14(2004).
32. You L, He B, Xu Z, et al. An anti-Wnt-2 monoclonal antibody induces apoptosis in malignant melanoma cells and inhibits tumor growth. *Cancer Res* 64:5385-9(2004).
33. Vincan E, Darcy P K, Smyth M J, et al. Frizzled-7receptor ectodomain expression in a colon cancer cell line induces morphological change and attenuates tumor growth. *Differentiation* 73:142-53(2005).
34. Zi X, Guo Y, Simoneau A R, et al. Expression of Frzb/secreted Frizzled-related protein 3, a secreted Wnt antagonist, in human androgen-independent prostate cancer PC-3 cells suppresses tumor growth and cellular invasiveness. *Cancer Res* 65:9762-70(2005).
35. Dennis S, Aikawa M, Szeto W, d'Amore P A, Papkoff J. A secreted frizzled related protein, FrzA, selectively associates with Wnt-1 protein and regulates wnt-1 signaling. *J Cell Sci* 112(Pt 21):3815-3820(1999).
36. Lu D, Zhao Y, Tawatao R, et al. Activation of the Wnt signaling pathway in chronic lymphocytic leukemia. *Proc Natl Acad Sci USA* 101:3118-23(2004).
37. Franke T F, Hornik C P, Segev L, Shostak G A, Sugimoto C. PI3K/Akt and apoptosis: size matters. *Oncogene* 22:8983-8998(2003).
38. Kurihara T, Brough D E, Kovesdi I, Kufe D W. Selectivity of a replication-competent adenovirus for human breast carcinoma cells expressing the MUC1 antigen. *J Clin Invest* 106:763-771(2000).
39. Zhou Z, Zhou R R, Guan H, Bucana C D, Kleinerman E S. E1A gene therapy inhibits angiogenesis in a Ewing's sarcoma animal model. *Mol Cancer Ther* 2:1313-9(2003).
40. Saito Y, Sunamura M, Motoi F, et al. Oncolytic replication-competent adenovirus suppresses tumor angiogenesis through preserved E1A region. *Cancer Gene Ther* 13:242-52(2006).
41. Sato H, Kida Y, Mai M, et al. Expression of genes encoding type IV collagen-degrading metalloproteinases and tissue inhibitors of metalloproteinases in various human tumor cells. *Oncogene* 7:77-83(1992).

What is claimed is:

1. A method for treating a cancer selected from the group consisting of stomach cancer, lung cancer, breast cancer, ovarian cancer, liver cancer, brain cancer, prostate cancer, sarcoma, nasopharyngeal cancer, laryngeal cancer, pancreatic cancer, bladder cancer, colon cancer, and uterine cervical cancer, the method comprising:

administering to a subject in need thereof a pharmaceutically effective amount of a composition comprising a nucleotide sequence encoding the amino acid sequence of SEQ ID NO:2.

2. The method according to claim 1, wherein the nucleotide sequence comprises SEQ ID NO: 1.

3. The method according to claim 1, wherein the nucleotide sequence is contained in a gene delivery system.

4. The method according to claim 3, wherein the gene delivery system is a plasmid, recombinant adenovirus, adeno-associated virus (AAV), retrovirus, herpes simplex virus, vaccinia virus, measles virus, poxvirus, Semliki Forest virus, polymer, nanomaterial, liposome, or niosome.

5. The method according to claim 4, wherein the gene delivery system is recombinant adenovirus.

6. The method according to claim 5, wherein the recombinant adenovirus comprises deleted E1B and E3 region and the nucleotide sequence of encoding the amino acid sequence of SEQ ID NO:2 is inserted into the deleted E1B and E3 region.

7. The method according to claim 1, wherein the cancer is lung cancer.

8. The method according to claim 1, wherein the composition inhibits activation of Wnt signaling pathway in a cancer cell.

9. The method according to claim 4, wherein the gene delivery system is adeno-associated virus.

10. The method according to claim 4, wherein the retrovirus is a lentivirus.

11. The method according to claim 1, wherein the cancer is selected from the group consisting of lung cancer, nasopharyngeal cancer, and laryngeal cancer.

* * * * *